United States Patent
Tabirian et al.

(10) Patent No.: US 11,366,253 B2
(45) Date of Patent: *Jun. 21, 2022

(54) DIFFRACTIVE WAVEPLATE LENSES AND APPLICATIONS

(71) Applicants: Beam Engineering for Advanced Measurements Co., Orlando, FL (US); U.S. Government as Represented by the Secretary of the Army, Natick, MA (US)

(72) Inventors: Nelson V. Tabirian, Winter Park, FL (US); Svetlana Serak, Oviedo, FL (US); Olena Uskova, Winter Park, FL (US); David E. Roberts, Apopka, FL (US); Anna Tabirian, Winter Park, FL (US); Diane Steeves, Franklin, MA (US); Brian Kimball, Shrewsbury, MA (US)

(73) Assignees: Beam Engineering for Advanced Measurements Co., Orlando, FL (US); U.S. Government as Represented by the Secretary of the Army, Natick, MA (US)

( * ) Notice: Subject to any disclaimer, the term of this patent is extended or adjusted under 35 U.S.C. 154(b) by 211 days.

This patent is subject to a terminal disclaimer.

(21) Appl. No.: 16/746,254

(22) Filed: Jan. 17, 2020

(65) Prior Publication Data

US 2020/0150323 A1 May 14, 2020

Related U.S. Application Data

(60) Division of application No. 16/220,995, filed on Dec. 14, 2018, now Pat. No. 10,557,977, which is a
(Continued)

(51) Int. Cl.
*G02B 6/12* (2006.01)
*G02B 6/32* (2006.01)
(Continued)

(52) U.S. Cl.
CPC .......... *G02B 5/1833* (2013.01); *A61F 2/1618* (2013.01); *A61F 2/1654* (2013.01);
(Continued)

(58) Field of Classification Search
CPC .... G02B 6/12004; G02B 6/32; G02B 5/3083; G02B 5/1833; G02B 5/0252;
(Continued)

(56) References Cited

U.S. PATENT DOCUMENTS 2,435,616 A 2/1948 Vittum
3,721,486 A 3/1973 Bramley
(Continued)

FOREIGN PATENT DOCUMENTS

EP 1970734 9/2008
EP 2088456 12/2009
(Continued)

OTHER PUBLICATIONS

Tabiryan, et al., The Promise of Diffractive Waveplates, OPN Optics and Photonics News, Mar. 2010, 6 pages.
(Continued)

*Primary Examiner* — Kaveh C Kianni
*Assistant Examiner* — Hung Q Lam
(74) *Attorney, Agent, or Firm* — Brian S. Steinberger; Hilary F. Steinberger; Law Offices of Brian S. Steinberger, P.A.

(57) ABSTRACT

Methods, systems and devices for diffractive waveplate lens and mirror systems allowing electronically pointing and focusing light at different focal planes. The system can be incorporated into a variety of optical schemes for providing
(Continued)

electrical control of transmission. In another embodiment, the system comprises diffractive waveplates of different functionality to provide a system for controlling not only focusing but other propagation properties of light including direction, phase profile, and intensity distribution. The diffractive waveplate lens and mirror systems are applicable to optical communication systems.

11 Claims, 26 Drawing Sheets

Related U.S. Application Data continuation-in-part of application No. 14/688,425, filed on Apr. 16, 2015, now Pat. No. 10,191,191, and a continuation-in-part of application No. 14/668,197, filed on Apr. 16, 2015, now Pat. No. 10,274,650, which is a continuation-in-part of application No. 13/916,627, filed on Jun. 13, 2013, now abandoned, which is a continuation-in-part of application No. 12/697,083, filed on Jan. 29, 2010, now abandoned.

(60) Provisional application No. 61/980,062, filed on Apr. 16, 2014.

(51) Int. Cl.

| | | |
|---|---|---|
| *G02B 6/30* | (2006.01) | |
| *G02B 6/028* | (2006.01) | |
| *G02B 6/10* | (2006.01) | |
| *G02B 5/18* | (2006.01) | |
| *G02C 7/02* | (2006.01) | |
| *G02C 7/06* | (2006.01) | |
| *G02C 7/12* | (2006.01) | |
| *A61F 2/16* | (2006.01) | |
| *G02B 3/10* | (2006.01) | |
| *G02C 7/08* | (2006.01) | |
| *G02B 5/30* | (2006.01) | |
| *G02B 27/42* | (2006.01) | |
| *G02B 5/00* | (2006.01) | |
| *G02B 6/024* | (2006.01) | |
| *G02B 6/35* | (2006.01) | |
| *G02B 3/00* | (2006.01) | |
| *G02C 7/10* | (2006.01) | |

(52) U.S. Cl.
CPC ............. *G02B 3/0081* (2013.01); *G02B 3/10* (2013.01); *G02B 5/001* (2013.01); *G02B 5/1828* (2013.01); *G02B 5/3083* (2013.01); *G02B 6/024* (2013.01); *G02B 6/3534* (2013.01); *G02B 6/3592* (2013.01); *G02B 27/4205* (2013.01); *G02B 27/4211* (2013.01); *G02B 27/4216* (2013.01); *G02B 27/4261* (2013.01); *G02C 7/022* (2013.01); *G02C 7/061* (2013.01); *G02C 7/086* (2013.01); *G02C 7/12* (2013.01); *G02C 7/10* (2013.01); *G02C 2202/16* (2013.01); *G02C 2202/20* (2013.01)

(58) Field of Classification Search
CPC .. G02B 5/1828; G02B 6/3534; G02B 6/3592; G02B 6/00; G02B 21/306; G02C 7/022; G02C 7/086
USPC ............... 385/11, 14, 33, 124, 129
See application file for complete search history.

(56) References Cited

U.S. PATENT DOCUMENTS

| | | |
|---|---|---|
| 3,897,136 A | 7/1975 | Bryngdahl |
| 4,160,598 A | 7/1979 | Firester et al. |
| 4,301,023 A | 11/1981 | Schuberth |
| 4,698,816 A | 10/1987 | Chun |
| 4,956,141 A | 9/1990 | Allen |
| 4,983,332 A | 1/1991 | Hahn |
| 5,032,009 A | 7/1991 | Gibbons |
| 5,042,950 A | 8/1991 | Salmon, Jr. |
| 5,047,847 A | 9/1991 | Toda |
| 5,100,231 A | 3/1992 | Sasnett et al. |
| 5,142,411 A | 8/1992 | Fiala |
| 5,150,234 A | 9/1992 | Takahashi |
| 5,218,610 A | 6/1993 | Dixon |
| 5,321,539 A | 6/1994 | Hirabayashi |
| 5,325,218 A | 6/1994 | Willett |
| 5,446,596 A | 8/1995 | Mostrorocco |
| 5,619,325 A | 4/1997 | Yoshida |
| 5,621,525 A | 4/1997 | Vogeler et al. |
| 5,712,721 A | 1/1998 | Large |
| 5,895,422 A | 4/1999 | Hauber |
| 5,903,330 A | 5/1999 | Funschilling |
| 5,907,435 A | 5/1999 | Ang |
| 5,989,758 A | 11/1999 | Komatsu |
| 6,091,471 A | 7/2000 | Kim |
| 6,107,617 A | 8/2000 | Love et al. |
| 6,139,147 A | 10/2000 | Zhang |
| 6,170,952 B1 | 1/2001 | La Haye et al. |
| 6,191,880 B1 | 2/2001 | Schuster |
| 6,219,185 B1 | 4/2001 | Hyde |
| 6,320,663 B1 | 11/2001 | Ershov |
| 6,373,549 B1 | 4/2002 | Tombling et al. |
| 6,452,145 B1 | 9/2002 | Graves et al. |
| 6,551,531 B1 | 4/2003 | Ford |
| 6,678,042 B2 | 1/2004 | Tabirian et al. |
| 6,728,049 B1 | 4/2004 | Tabirian et al. |
| 6,792,028 B2 | 9/2004 | Cook |
| 6,911,637 B1 | 6/2005 | Vorontsov et al. |
| 7,048,619 B2 | 5/2006 | Park |
| 7,072,086 B2 * | 7/2006 | Batchko .................. G02B 5/32 359/15 |
| 7,094,304 B2 | 8/2006 | Nystrom |
| 7,095,772 B1 | 8/2006 | Delfyett et al. |
| 7,196,758 B2 | 3/2007 | Crawford |
| 7,319,566 B2 | 1/2008 | Prince |
| 7,324,286 B1 | 1/2008 | Glebov |
| 7,450,213 B2 | 11/2008 | Kim et al. |
| 7,482,188 B2 | 1/2009 | Moon |
| 7,764,426 B2 | 7/2010 | Lipson |
| 8,045,130 B2 | 10/2011 | Son |
| 8,077,388 B2 | 12/2011 | Gerton |
| 8,264,623 B2 | 9/2012 | Marrucci |
| 8,520,170 B2 | 8/2013 | Escuti |
| 8,582,094 B1 | 11/2013 | Shortt |
| 8,643,822 B2 | 2/2014 | Tan et al. |
| 8,937,701 B2 | 1/2015 | Rossini |
| 8,982,313 B2 | 3/2015 | Escuti et al. |
| 9,535,258 B1 | 1/2017 | Whiteaker |
| 9,541,772 B2 | 1/2017 | De Sio et al. |
| 9,557,456 B2 | 1/2017 | Tabirian et al. |
| 9,592,116 B2 | 3/2017 | De Sio et al. |
| 9,617,205 B2 | 4/2017 | Tabirian et al. |
| 9,658,512 B2 | 5/2017 | Tabirian et al. |
| 9,715,048 B2 | 7/2017 | Tabirian et al. |
| 9,753,193 B2 | 9/2017 | Tabirian et al. |
| 9,976,911 B1 | 5/2018 | Tabirian et al. |
| 9,983,479 B2 | 5/2018 | Tabirian et al. |
| 10,031,424 B2 | 7/2018 | Tabirian et al. |
| 10,036,886 B2 | 7/2018 | Tabirian et al. |
| 10,075,625 B2 | 9/2018 | Tabirian et al. |
| 10,107,945 B2 | 10/2018 | Tabirian et al. |
| 10,114,239 B2 | 10/2018 | Tabirian et al. |
| 10,120,112 B2 | 11/2018 | Tabirian et al. |
| 10,185,182 B2 | 1/2019 | Tabirian |
| 10,191,191 B2 | 1/2019 | Tabirian et al. |
| 10,191,296 B1 | 1/2019 | Tabirian et al. |

(56) References Cited

U.S. PATENT DOCUMENTS

| | | |
|---|---|---|
| 10,197,715 B1 | 2/2019 | Tabirian et al. |
| 10,274,650 B2 | 4/2019 | Tabirian et al. |
| 10,330,947 B2 | 6/2019 | Tabirian et al. |
| 10,423,045 B2 | 9/2019 | Tabirian et al. |
| 10,436,957 B2 | 10/2019 | Tabirian et al. |
| 2001/0002895 A1 | 6/2001 | Kawano |
| 2001/0018612 A1 | 8/2001 | Carson et al. |
| 2001/0030720 A1 | 10/2001 | Ichihashi |
| 2002/0027624 A1 | 3/2002 | Seiberle |
| 2002/0097361 A1 | 7/2002 | Ham |
| 2002/0167639 A1 | 11/2002 | Coates |
| 2003/0021526 A1 | 1/2003 | Bouevitch |
| 2003/0072896 A1 | 4/2003 | Kwok |
| 2003/0137620 A1 | 7/2003 | Wang |
| 2003/0152712 A1 | 8/2003 | Motomura |
| 2003/0206288 A1 | 11/2003 | Tabirian et al. |
| 2003/0214700 A1 | 11/2003 | Sidorin |
| 2003/0218801 A1 | 11/2003 | Korniski et al. |
| 2004/0051846 A1 | 3/2004 | Blum et al. |
| 2004/0081392 A1 | 4/2004 | Li |
| 2004/0105059 A1 | 6/2004 | Ohyama |
| 2004/0165126 A1 | 8/2004 | Ooi et al. |
| 2005/0030457 A1 | 2/2005 | Kuan et al. |
| 2005/0110942 A1 | 5/2005 | Ide |
| 2005/0219696 A1 | 10/2005 | Albert et al. |
| 2005/0271325 A1 | 12/2005 | Anderson et al. |
| 2005/0276537 A1 | 12/2005 | Frisken |
| 2005/0280717 A1 | 12/2005 | Chen |
| 2006/0008649 A1 | 1/2006 | Shinichiro |
| 2006/0055883 A1 | 3/2006 | Morris et al. |
| 2006/0109532 A1 | 5/2006 | Savas |
| 2006/0221449 A1 | 10/2006 | Glebov et al. |
| 2006/0222783 A1 | 10/2006 | Hayashi |
| 2007/0032866 A1 | 2/2007 | Portney |
| 2007/0040469 A1 | 2/2007 | Yacoubian |
| 2007/0115551 A1 | 5/2007 | Spilman |
| 2007/0122573 A1 | 5/2007 | Yasuike |
| 2007/0132930 A1 | 6/2007 | Ryu et al. |
| 2007/0247586 A1 | 10/2007 | Tabirian |
| 2007/0258677 A1 | 11/2007 | Chigrinov |
| 2008/0226844 A1 | 9/2008 | Shemo |
| 2008/0278675 A1 | 11/2008 | Escuti |
| 2009/0002588 A1 | 1/2009 | Lee et al. |
| 2009/0052838 A1 | 2/2009 | McDowall |
| 2009/0073331 A1 | 3/2009 | Shi |
| 2009/0122402 A1 | 5/2009 | Shemo |
| 2009/0141216 A1 | 6/2009 | Marrucci |
| 2009/0201572 A1 | 8/2009 | Yonak |
| 2009/0256977 A1 | 10/2009 | Haddock |
| 2009/0257106 A1 | 10/2009 | Tan |
| 2009/0264707 A1 | 10/2009 | Hendricks |
| 2010/0003605 A1 | 1/2010 | Gil |
| 2010/0066929 A1 | 3/2010 | Shemo |
| 2010/0245954 A1 | 9/2010 | Ahling |
| 2011/0069377 A1 | 3/2011 | Wu et al. |
| 2011/0075073 A1 | 3/2011 | Oiwa |
| 2011/0085117 A1 | 4/2011 | Moon et al. |
| 2011/0097557 A1 | 4/2011 | May |
| 2011/0109874 A1 | 5/2011 | Piers et al. |
| 2011/0135850 A1 | 6/2011 | Saha et al. |
| 2011/0188120 A1 | 8/2011 | Tabirian et al. |
| 2011/0234944 A1 | 9/2011 | Powers |
| 2011/0262844 A1 | 10/2011 | Tabirian |
| 2012/0075168 A1 | 3/2012 | Osterhout et al. |
| 2012/0140167 A1 | 6/2012 | Blum |
| 2012/0162433 A1 | 6/2012 | Fuentes Gonzalez |
| 2012/0188467 A1 | 7/2012 | Escuti |
| 2013/0057814 A1 | 3/2013 | Prushinskiy et al. |
| 2013/0202246 A1 | 8/2013 | Meade |
| 2014/0055740 A1 | 2/2014 | Spaulding |
| 2014/0211145 A1 | 7/2014 | Tabirian |
| 2014/0252666 A1 | 9/2014 | Tabirian |
| 2015/0049487 A1 | 2/2015 | Connor |
| 2015/0081016 A1 | 3/2015 | De Sio et al. |
| 2015/0276997 A1 | 10/2015 | Tabirian et al. |
| 2016/0011564 A1 | 1/2016 | Tanabe et al. |
| 2016/0023993 A1 | 1/2016 | Tabirian |
| 2016/0047955 A1 | 2/2016 | Tabirian et al. |
| 2016/0047956 A1 | 2/2016 | Tabirian et al. |
| 2016/0209560 A1 | 7/2016 | Tabirian et al. |
| 2016/0231592 A9 | 8/2016 | Beaton et al. |
| 2016/0270656 A1 | 9/2016 | Samec et al. |
| 2016/0363484 A1 | 12/2016 | Barak et al. |
| 2016/0363783 A1 | 12/2016 | Blum |
| 2017/0010397 A1 | 1/2017 | Tabirian et al. |
| 2019/0113777 A1 | 4/2019 | Tabirian et al. |

FOREIGN PATENT DOCUMENTS

| | | |
|---|---|---|
| GB | 2209751 | 5/1989 |
| JP | 2001142033 | 5/2001 |
| JP | 2004226752 | 8/2004 |
| WO | 2007122573 | 11/2007 |
| WO | 2008130555 | 10/2008 |
| WO | 2008130559 | 10/2008 |

OTHER PUBLICATIONS

Tabiryan, et al., Fabricating Vector Vortex Waveplates for Coronagraphy; Aerospace Conference, 2012, EEE; publicly available Apr. 19, 2012, 12 pages.

Tabirian, et al., PCT Application No. PCT/US15/26186 filed Apr. 16, 2015, Notification of Transmittal of the International Search Report and the Written Opinion of the International Searching Authority dated Jul. 14, 2015, 17 pages.

Nersisyan, et al., Study of azo dye surface command photoalignment material for photonics applications, Applied Optics, vol. 49, No. 10, Apr. 1, 2010, 8 pages.

Nersisyan, et al., Characterization of optically imprinted polarization gratings, Applied Optics, vol. 48, No. 21, Jul. 20, 2009, 6 pages.

Nersisyan, et al., Fabrication of Liquid Crystal Polymer Axial Waveplates for UV-IR Wavelengths, Optics Express, vol. 17, No. 14, Jul. 2009, 9 pages.

Nersisyan, et al., Optical Axis Gratings in Liquid Crystals and Their Use for Polarization Insensitive Optical Switching, Journal of Nonlinear Optical Physics & Materials, vol. 18, No. 1, 2009, 47 pages.

Nersisyan, et al., Polarization insensitive imaging through polarization gratings, Optics Express, vol. 17. No. 3, Feb. 2, 2009, 14 pages.

Sarkissian, et al., Longitudinally modulated nematic bandgap structure, Optical Society of America, vol. 23, No. 8, Aug. 2008, 6 pages.

Sarkissian, et al., Polarization-universal bandgap in periodically twisted nematics, Optics Letters, vol. 31, No. 11, Jun. 1, 2006, abstract, 4 pages.

Sarkissian, et al., Periodically Aligned Liquid Crystal: Potential Application for Projection Displays, Mol. Cryst. Liq. Cryst., vol. 451, 2006, 19 pages.

Sarkissian, et al., Potential application of Periodically Aligned Liquid Crystal cell for projection displays, JThE12, 2005, 3 pages.

Sarkissian, et al., Polarization-Controlled Switching Between Diffraction Orders in Transverse-Periodically Aligned Nematic Liquid Crystals, Optics Letters, Aug. 2006, abstract, 4 pages.

Schadt, et al., Photo-Induced Alignment and Patterning of Hybrid Liquid Crystalline Polymer Films on Single Substrates, Jpn. J. Appl. Phys., vol. 34, Part 2, No. 6B, Jun. 15, 1995, 4 pages.

Schadt, et al., Photo-Generation of Linearly Polymerized Liquid Crystal Aligning Layers Comprising Novel, Integrated Optically Patterned Retarders and Color Filters, Jpn. J. Appl. Phys., vol. 34, Part 1, No. 6A, Jun. 1995, 10 pages.

Schadt, et al., Optical patterning of multi-domain liquid-crystal displays with wide viewing angles, Nature, vol. 381, May 16, 1996, 4 pages.

Escuti, et al., A Polarization-Independent Liquid Crystal Saptial-Light-Modulator, Liquid Crystals X, Proc. of SPIE, vol. 6332, 2006, 9 pages.

Escuti, et al., Polarization-Independent LC Microdisplays Using Liquid Crystal Polarization Gratings: A Viable Solution (?), Dept of Electrical & Computer Engineering @ ILCC, Jul. 1, 2008, 30 pages.

(56) References Cited

OTHER PUBLICATIONS

Escuti, et al., Simplified Spectropolarimetry Using Reactive Mesogen Polarization Gratings, Imaging Spectrometrv XI, Proc. of SPIE, vol. 6302, 2006, 11 pages.
Gibbons, et al., Surface-mediated alignment of nematic liquid crystals with polarized laser light, Nature, vol. 351, May 2, 1991, 1 page.
Gibbons, et al., Optically Controlled Alignment of Liquid Crystals: Devices and Applications, Molecular Crystals and Liquid Crystals, vol. 251, 1994, 19 pages.
Gibbons, et al., Optically generated liquid crystal gratings, Appl. Phys. Lett., 65, Nov. 14, 1994, 3 pages.
University of Central Fiorida, School of Optics CREOL PPCE, Optics in the Southeast, Technical Conference and Tabletop Exhibit, Nov. 12-13, 2003, 9 pages.
Ichimura, et al., Surface assisted photoalignment contiol of lyotropic liquid crystals, Part 1, Characterization and photoalignment of aqueous solutions of a water soluble dyes as lyotropic liquid crystals, J. Materials. Chem., vol. 12, 2002, abstract, 2 pages.
Ichimura, et al., Reversible Change in Alignment Mode of Nematic Liquid Crystals Regulated Photochemically by "Command Surfaces" Modified with an Azobenzene Monolayer, American Chemical Society, Langmuir, vol. 4, No. 5, 1988, 3 pages.
Zel'dovich, et al., Devices for displaying visual information, Disclosure, School of Optics/CREOL, University of Central Florida, Jul. 2000, 10 pages.
Provenzano, et al., Highly efficient liquid crystal based diffraction grating induced by polarization holograms at the aligning surfaces, Applied Physics Letter 89, 2006, 4 pages.
Titus, et al., Efficient polarization-independent, re ective liquid crystal phase grating, Applied Physics Letter 71, Oct. 20, 1197, 3 pages.
Chen, et al. An Electrooptically Controlled Liquid-Crystal Diffraction Grating, Applied Physics Letter 67, Oct. 30, 1995, 4 pages.
Kim et al., Unusual Characteristics of Diffraction Gratings in a Liquid Crystal Cell, Advanced Materials, vol. 14, No. 13-14, Jul. 4, 2002, 7 pages.
Pan, et al., Surface Topography and Alignment Effects in UV-Modified Polyimide Films with Micron Size Patterns, Chinese Journal of Physics, vol. 41, No. 2, Apr. 2003, 8 pages.
Fuh, et al., Dynamic studies of holographic gratings in dye-doped liquid-crystal films, Optics Letter, vol. 26, No. 22, Nov. 15, 2001, 3 pages.
Yu, et al., Polarization Grating of Photoaligned Liquid Crystals with Oppositely Twisted Domain Structures, Molecular Crystals Liquid Crystals, vol. 433, 2005, 7 pages.
Crawford, et al., Liquid-crystal diffraction gratings using polarization holography alignment techniques, Journal of Applied Physics 98, 2005, 10 pages.
Seiberle, et al., 38.1 Invited Paper: Photo-Aligned Anisotropic Optical Thin Films, SID 03 Digest, 2003, 4 pages.
Wen, et al., Nematic liquid-crystal polarization gratings by modification of surface alignment. Applied Optics, vol. 41. No. 7, Mar. 1, 2002, 5 pages.
Anagnostis, et al., Replication produces holographic optics in volume, Laser Focus World, vol. 36, Issue 3, Mar. 1, 2000, 6 pages.
Gale, Replicated Diffractive Optics and Micro-Optics, Optics and Photonics News, Aug. 2003, 6 pages.
McEldowney, et al., Creating vortex retarders using photoaligned LC polymers, Optics Letter, vol. 33, No. 2, Jan. 15, 2008, 3 pages.
Stalder, et al., Lineraiy polarized light with axial symmetry generated by liquid-crystal polarization converters, Optics Letters vol. 21, No. 1996, 3 pages.
Kakichashvili, et al., Method for phase polarization recording of holograms, Sov. J. Quantum. Electron, vol. 4, No. 6, Dec. 1974, 5 pages.
Todorov, et al., High-Sensitivity Material With Reversible Photo-Induced Anisotropy, Optics Communications, vol. 47, No. 2, Aug. 15, 1983, 4 pages.

Attia, et al., Anisoptropic Gratings Recorded From Two Circularly Polarized Coherent Waves, Optics Communications, vol. 47, No. 2, Aug. 15, 1983, 6 pages.
Cipparrone, et al., Permanent polarization gratings in photosensitive langmuir blodget films, Applied Physics Letter, vol. 77, No. 14, Oct. 2, 2000, 4 pages.
Nikolova, et al., Diffraction Efficiency and Selectivity of Polarization Holographic Recording, Optica Acta: International Journal of Optics, vol. 31, No. 5, 1984, 11 pages.
Lee et al. "Generation of pretilt angles of liquid crystals on cinnamte-based photoalignment . . . ", Opt., Expr., vol. 17 (26) (Dec. 2009), abstract, 4 pages.
Yaroshchuk et al. "Azodyes as photoalignment agents for polymerizable liquid crystals", IDW'06 Digest vol. 1 -3, 2006, 4 pages.
Chigrinov et al. "Anchoring properties of photoaligned azo-dye materials" Phys. Rev., E vol. 68, (Dec. 2003), 5 pages.
Pagliusi et al. Surface-induced photorefractivity in twistable nematics: toward the all-optical control of gain, Opt. Expr. vol. 16, Oct. 2008, 9 pages.
M. Honma, T. Nose, Polarization-independent liquid crystal grating fabricated by microrubbing process, Jpn. J. Appl. Phys., Part 1, vol. 42, 2003, 3 pages.
Anderson, G., et al., Broadband Antihole Photon Sieve Telescope, Applied Optics, vol. 16, No. 18., Jun. 2007, 3 pages.
Early, J. et al., Twenty Meter Space Telescope Based on Diffractive Fresnel Lens, SPIE, U.S. Department of Energy, Lawrence Livermore National Laboratory, Jun. 2003, 11 pages.
Martinez-Cuenca, et al., Reconfigurable Shack-Hartmann Sensor Without Moving Elements,Optical Society of America, vol. 35, No. 9, May 2010, 3 pages.
Serak, S., et al., High-efficiency 1.5 mm Thick Optical Axis Grating and its Use for Laser Beam Combining, Optical Society of America, vol. 32, No. Jan. 2007, 4 pages.
Ono et al., Effects of phase shift between two photoalignment substances on diffration properties in liquid crystalline grating cells, Appl. Opt. vol. 48, Jan. 2009, 7 pgs.
Naydenova et al., "Diffraction form polarization holographic gratings with surface relief in side chain azobenzene polyesters" J. Opt. Soc. Am. B, vol. 15, (1998), 14 pages.
Oh et al., Achromatic polarization gratings as highly efficent thin-film polarizing beamsplitters for broadband light Proc. SPIE vol. 6682, (2007), 4 pages.
Nersisyan, S., et al., Polarization insensitive imaging through polarization gratins, Optics Express, vol. 17, No. 3, Feb. 2, 2009, 14 pages.
OISE, Optics in the Southeast, Technical Conference and Tabletop Exhibit, Optical Society of America, Orlando, FL., Nov. 12-13, 2003, 9 pages.
Dierking, Polymer Network-Stabilized Liquid Crystals, Advanced Materials, vol. 12, No. 3, 2000, 15 pages.
Tabiryan, et al., Broadband waveplate lenses, Optics Express 7091, vol. 24, No. 7, Mar. 24, 2016, 12 pages.
Tabiryan, et al. Thin waveplate lenses of switchable focal length—new generation in optics, Optics Express 25783, vol. 23, No. 20, Sep. 19, 2015, 12 pages.
Tabiryan, et al. Superlens in the skies: liquid-crystal-polymer technology for telescopes, Newsroom, 2016, 2 pages.
Nersisyan, et al., The principles of laser beam control with polarization gratings introduced as diffractive waveplates, Proc. of SPIE, vol. 7775, 2010, 10 pages.
Heller, A Giant Leap for Space Telescopes, Foldable Optics, S&TR, Mar. 2003, 7 pages.
Beam Engineering For Advanced Measurements Co., PCT Application No. PCT/US2015026186, The Extended European Search Report, filed on Mar. 8, 2017, 13 pages.
Blinov, et al., Electrooptic Effects in Liquid Crystal MAterials, Springer-Verlag New York, 1994, 17 pages.
Crawford, et al., Liquid Crystals in Complex Geometries; Formed by Polymer and Porous Networks, Taylor and Francis, 1996, 4 pages.
Honma, et al., Liquid-Crystal Fresnel Zone Plate Fabricated by Microorubbing, Japanese Journal of Applied Phsyics, vol. 44, No. 1A, 2005, 4 pages.

(56) References Cited

OTHER PUBLICATIONS

Tabirian, N., et al., U.S. Appl. No. 61/757,259, filed Jan. 28, 2013, 29 pages.

Beam Engineering for Advaced Measurements Co., et al., PCT Application No. PCT/US2016/038666 filed Jun. 22, 2016, Notification of Transmittal of the International Search Report and the Written Opinion of the International Searching Authority, or the Declaration dated Oct. 10, 2016, 16 pages.

Marrucci, et al., Pancharatnam-Berry phase optical elements for wave front shaping in the visible domain, Appl. Phys. Lett. 88, 2006, 3 pages.

Sobolewska et al., "On the inscription of period and half period surface relief gratings in azobenzene-functionalized polymers", J. Phys. Chem., vol. 112 (15) Jan. 3, 2008, 10 pages.

Barrett et al., Model of laser driven mass transport in thin films of dye-functionalized polymers, J. Chem. Phys., vol. 109 (4), Jul. 22, 1998, 13 pages.

Vernon, J., et al., Recording Polarization Gratings with a Standing Spiral Wave, Applied Physics Letters, Oct. 2013, vol. 103, 4 pages.

Gerchberg, et al, practical algorithm for the determination of the phase from image and diffraction plane pictures, 1972, Optik, vol. 35, Issue 2, pp. 237-246, 10 pages.

Serak, et al. Diffractive Waveplate Arrays [Invited], Journal of the Optical Society of America B, May 2017, pp. B56-B63, vol. 34, No. 5, 8 pages.

Emoto, Optical and Physical Applications of Photocontrollable Materials: Azobenzene-Containing and Liquid Crystalline Polymers, Polymers,Jan. 2012, 150-186, vol. 4, 38 pages.

Pepper, M. et al., Nonlinear Optical Phase Conjugation, IEEE, Sep. 1991, pp. 21-34, 14 pages.

De Sio, L., et al., "Digital Polarization Holography Advancing Geometrical Phase Optics," 2016, Optics Express, vol. 24, Issue 16, pp. 18297-18306, 10 pages.

Borek, G. and D. Brown, "High-performance diffractive optics for beam shaping," 1999, Proceeding of SPIE, vol. 3633, pp. 51-60, 10 pages.

Roberts, D. et al., "Polarization-Independent Diffractive Waveplate Optics," Mar. 2018, IEEE Aerospace Conference, 11 pages.

\* cited by examiner

DIFFRACTIVE WAVEPLATE LENSES AND APPLICATIONS

CROSS REFERENCE TO RELATED APPLICATIONS

This application is a divisional of U.S. patent application Ser. No. 16/220,995 filed Dec. 14, 2018, now U.S. Pat. No. 10,557,977, which is a Continuation of U.S. patent application Ser. No. 14/688,425 filed Apr. 16, 2015, now U.S. Pat. No. 10,191,191, which claims the benefit of priority to U.S. Provisional Application Ser. No. 61/980,062 filed Apr. 16, 2014, and U.S. patent application Ser. No. 16/220,995 filed Dec. 14, 2018, now allowed, which is a Continuation-In-Part of U.S. patent application Ser. No. 14/688,197 filed Apr. 16, 2015, now U.S. Pat. No. 10,274,650, which claims the benefit of priority to U.S. Provisional Patent Application Ser. No. 61/980,062 filed Apr. 16, 2014, and U.S. patent application Ser. No. 14/688,197 filed Apr. 16, 2015 now U.S. Pat. No. 10,274,650, is a Continuation-In-Part of U.S. patent application Ser. No. 13/916,627 filed Jun. 13, 2013, which is a Continuation of U.S. patent application Ser. No. 12/697,083 filed Jan. 29, 2010. The entire disclosure of the applications listed in this paragraph are incorporated herein by specific reference thereto.

GOVERNMENT LICENSE RIGHTS

This invention was made with government support under Contract No. W911QY-12-C-0016. The government has certain rights in this invention.

FIELD OF INVENTION

This invention relates to optical lenses, the method of their fabrication, applications of the lenses, and applications of combinations of said lenses with application of said lenses including imaging optics and systems, astronomy, displays, polarizers, optical communication and other areas of laser and photonics technology.

BACKGROUND AND PRIOR ART

The present invention is in the technical field of optics. More particularly, the present invention is in the technical field of lenses. Lenses are commonly made by shaping an optical material such as glass. The weight of such lenses increases strongly with diameter making them expensive and prohibitively heavy for applications requiring large area. Also, the quality of a lens typically decreases with increasing size. To achieve desired features such as high-quality imaging, conventional lenses sometimes have curved surfaces that are non-spherical. The need to grind and polish conventional lenses with non-spherical surfaces can make such lenses extremely expensive. Segmented lenses such as Fresnel lenses are relatively thin, however, the structural discontinuities result in severe aberrations. Uses of holographic lenses are limited by the compromise of efficiency, spectral bandwidth and dispersion. Thus, there is a need for lenses that could be obtained in the form of thin film structurally continuous coatings on a variety of substrates.

Thus, the need exists for solutions to the above problems with the prior art.

SUMMARY OF THE INVENTION

The objective of the present invention is providing a lens with continuous thin film structure whose properties can be changed in a useful way by application of an electrical potential to the lens.

The second objective of the present invention is providing a combination of lenses with spherically symmetric continuous thin film structure such that the properties of the individual lenses are changed by means of the application of an electrical potential, in such a way that the combination of lenses allows the focal position of an imaging system to be adjusted among a multiplicity of possible focal positions.

The third objective of the present invention is providing combinations of lenses, each with a continuous thin film structure, such that one or more of the lenses are controlled by means of the application of an electrical potential, and such that by means of electrical switching of these lenses, coupling between optical fibers can be turned on or off.

The fourth objective of the present invention is providing a variable attenuator of electromagnetic radiation using an electrically-controlled thin-film structure.

Many of the exemplary applications have been described herein with terms such as "light" being used to describe the electromagnetic radiation that is acted upon by the disclosed diffractive waveplate lenses. The term "light" in this context should not be taken to restrict the scope of the disclosed embodiments to only those in which the electromagnetic radiation acted upon or manipulated by the diffractive waveplate lenses is in the visible region of the spectrum. As will be evident to those skilled in the art, the exemplary embodiments disclosed here, in addition to being applicable in the visible region of the spectrum, are equally applicable to the microwave, infrared, ultraviolet, and X-ray regions of the spectrum. Exceptions to this generalization are the applications relating to human vision, for which operation in the visible region of the spectrum is required.

The design and function of the optical lenses of the present invention have not been suggested, anticipated or rendered obvious by any of the prior art references.

Further objects and advantages of this invention will be apparent from the following detailed description of the presently preferred embodiments which are illustrated schematically in the accompanying drawings.

DESCRIPTION OF THE PREFERRED EMBODIMENTS

Figure 1A:
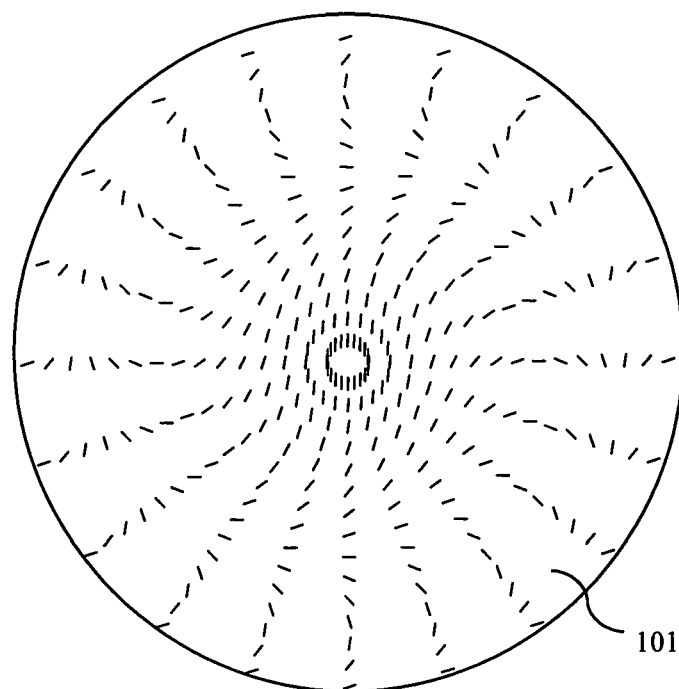
FIG. 1A shows spatial distribution of optical axis orientation in spherical diffractive waveplate lenses of one sign.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

A list of components will now be described.
101 left hand thin film diffractive waveplate lens
102 right hand thin film diffractive waveplate lens
201 continuous lines
300 plane
301 observer
302 observer
400 component/element
410 right-hand circular polarized (RHCP) light beam
411 defocused RHCP light beam
412 focused RHCP light beam
420 left-hand circular polarized (LHCP) light beam
421 defocused (LHCP) light beam
422 focused LHCP beam
430 DWL layer
440 substrate
601 collimated lens beams
602 lens 603 focal region
612 aspheric lens
613 focal region
614 diffractive waveplate lens
615 diffractive waveplate lens
616 diffractive waveplate lens
617 incoming beam
618 conventional lens
619 diffractive waveplate lens
620 focal region
701 collimated beam
702 optical system axis
703 right-hand circular polarized beam
704 left-hand circular polarized beam
711 diffractive waveplate lens
712 diffractive waveplate lens
721 focal region
801 diffractive waveplate lens
802 diffractive waveplate lens
803 diffractive waveplate lens
804 cone of light
805 focal point
901 collimated beam
902 optical system axis
903 spherical lens
904 RHCP component
905 LHCP red beam
906 focal point
907 RHCP component of blue light
908 LHCP component of blue light
909 focal point
1001 diffractive waveplate lens
1002 diffractive waveplate lens
100 diffractive waveplate lens
1010 focal point
1101 collimated light beam
1102 optical system axis
1103 diffractive waveplate lens
1104 focal point
1120 non-diffracted collimated beam
1105 focused beam
1120 non-diffractive collimated beam
1201 beam
1202 axis
1203 lens
1204 diffractive waveplate lens
1205 diffractive waveplate lens
1210 focal plane
1220 focal plane
1230 focal plane
1240 focal plane
1301 fiber optic
1302 tip of 1301
1303 light cone
1304 diffractive waveplate lens
1305 diffractive waveplate lens
1306 diffractive waveplate lens
1307 converging cone
1308 tip of 1309
1309 fiber optic
1310 beam block
1311 diverging beam
1320 fiber optic
1321 diffractive waveplate lens
1322 defocused beam
1323 focused beam
1401 diffractive waveplate lens
1402 diffractive waveplate lens
1403 diffractive waveplate lens
1404 polarization switching components
1405 cycloidal diffractive waveplate
1406 vector vortex waveplate
1407 cylindrical diffractive waveplate lens
1408 cylindrical diffractive waveplate lens
1409 polarization switching components (switchable phase retardation layer)
1410 polarization switching components (switchable phase retardation layer)
1411 cylindrical diffractive waveplate lens
1412 cylindrical diffractive waveplate lens
1501 electrodes for application of electric field
1502 substrate
1503 substrate
1504 electro-optical material
1505 diffractive waveplate film
1602 diffractive waveplate film
1603 variable phase retardation film
1604 mirror
1605 focused beam Glossary of Terms:

Diffractive waveplates (DWs): A birefringent film with anisotropy axis orientation modulated in the plane of the film. Different modulation patterns are possible resulting in different optical functionality, including lens, prism, axicon, etc. Generally, DWs may possess more than one layer, and the anisotropy axis may be modulated also in the bulk of the layer.

Diffractive waveplate lens: A diffractive waveplate with lens function. It may provide spherical, cylindrical, and other types of lens action.

Optical substrate or optical film A transparent material providing mechanical support for DWs. It may be glass, quartz, plastic, or any other material that is at least partially transparent for the wavelengths of light that propagate through the DWs. It may possess anti-reflective or anti-scratch functions.

Switchable Diffractive waveplate: A DW that can be switched between diffractive and non-diffractive states upon application of external influences such as electric fields, temperature, optical radiation, etc. Generally, the switching can take place through gradual change of diffraction spectrum.

Variablephase retarder or polarization controller: An optical component capable of controlling the polarization of light propagated through it by applying electric fields, changing temperature, exposure to a light beam, etc. Particularly, it may be a liquid crystal sandwiched between substrates coated with transparent electrodes.

Before explaining the disclosed preferred embodiments of the present invention in detail it is to be understood that the invention is not limited in its application to the details of the particular arrangements shown since the invention is capable of other embodiments. Also, the terminology used herein is for the purpose of description and not limitation.

In the description here of the invention, the term "light" will often be used to describe the electromagnetic radiation that interacts with the diffractive waveplate lenses that are subject of this invention. Although "light" generally means electromagnetic radiation with a wavelength in the visible region of the electromagnetic radiation with a wavelength in the visible region of the electromagnetic spectrum, it should be understood that the usage of the term "light" in the description is not restrictive, in the sense of limiting the design and application to diffractive waveplate lenses that operate only in the visible region of the spectrum. In general, all the designs and concepts described herein apply to operation over a wide range of the electromagnetic spectrum, including the microwave, infrared, visible, ultraviolet, and X-ray regions. While physical embodiments of diffractive waveplate lenses are at present advanced for operation in the visible region of the spectrum, the designs and applications disclosed here are applicable over all the noted regions of the electromagnetic spectrum.

The present invention relates to the design and application of diffractive waveplate lenses. The term "diffractive waveplate lens" as used herein describes a thin film of birefringent material deposited on a transparent structure, for example, a thin flat substrate of optical material such as glass. This birefringent film has the property that it retards the phase of light of one linear polarization by approximately one half wave (pi radians of optical phase) relative to the light of the other linear polarization. In diffractive waveplate lenses, the optical axis orientation depends on the transverse position on the waveplate, i.e. the position in the two coordinate axes perpendicular to the surface of the diffractive waveplate lens. In other words, the optical axis orientation is modulated in one or both of the transverse directions parallel to the surface of the substrate on which the active thin film is applied. Lensing action is due to parabolic profile of optical axis orientation modulation.

There are two general types of diffractive waveplate lenses to which the present invention applies. The first type of diffractive waveplate lens is axially symmetric and is used, for example, to focus a collimated beam of light to a point in space. The second type of diffractive waveplate lens is cylindrically symmetric and is used, for example, to focus a collimated beam of light to a line segment in space. In many examples below, an optical system of circular symmetry is used as an example, but in general, all of the conclusions apply as well to optical systems of cylindrical symmetry.

Figure 1B:
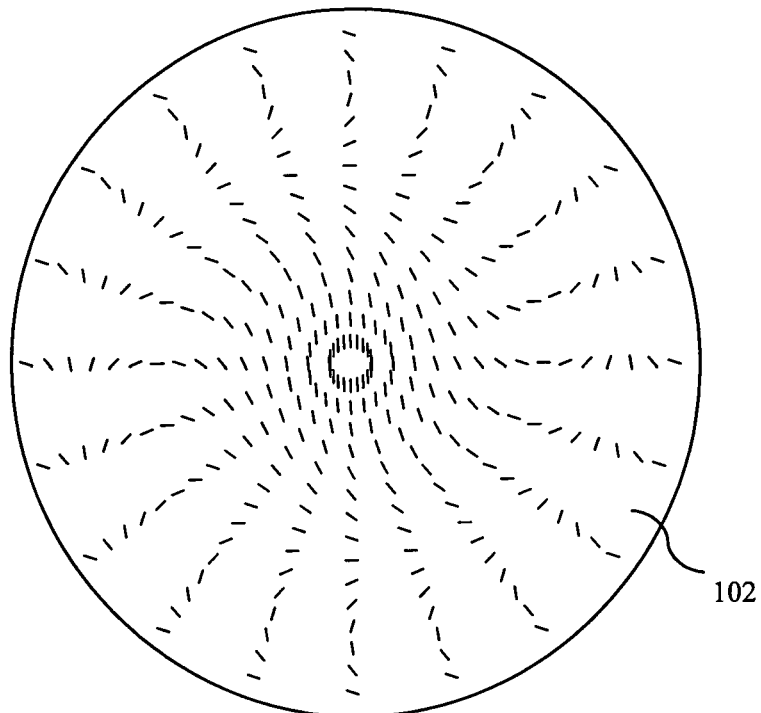
FIG. 1B shows spatial distribution of optical axis orientation in spherical diffractive waveplate lenses of an opposite sign.

In FIG. 1, the orientation of the anisotropy axis at each point of the birefringent thin film 101 is indicated by a short line segments. In the first type of diffractive waveplate lenses to which the present invention applies, illustrated in FIG. 1A, the orientation of the anisotropy axis of the birefringent material comprising the thin film layer depends only on the radial distance r from a center point. This type of spherical diffractive waveplate lens is used for applications such as focusing a collimated beam of light to a point for imaging a distant scene onto a sensor array. To perform this function, the angle α that the anisotropy axis of the birefringent material makes with the coordinate axis is given by the following equation:

$$\alpha = \pm \frac{k_0}{4f} r^2$$

where $k_0 = 2\pi/\lambda$ is the wavenumber of the light that is to be focused by the diffractive waveplate lens, $\lambda$ is the wavelength of that radiation, f is the focal length of the diffractive waveplate lens (DWL), and r is the distance to the central point.

Figure 2A:
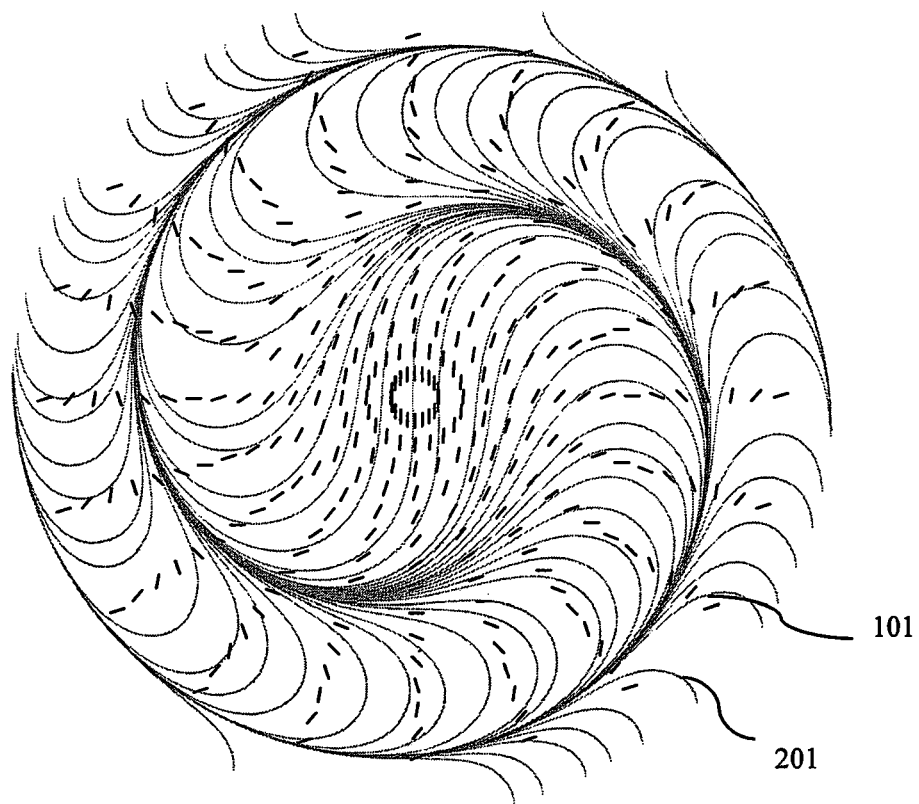
FIG. 2A shows a representation of a spherical diffractive waveplate lens with continuous alignment lines of anisotropy axis of the birefringent material.
Figure 2B:
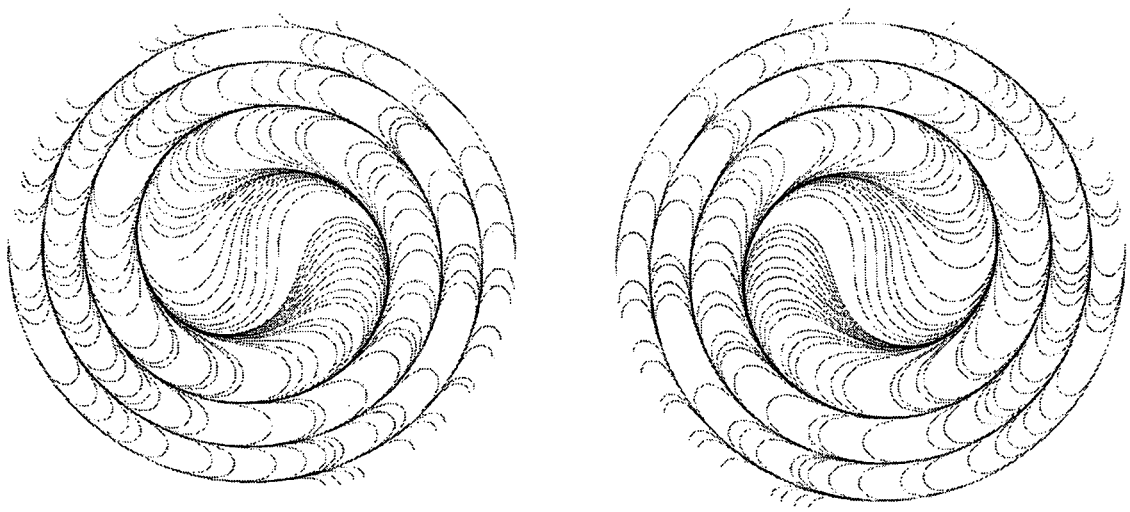
FIG. 2B shows spherical diffractive waveplate lenses of opposite signs in description with continuous alignment lines.

The difference in signs in variation of the anisotropy axis with radius designate lenses of two opposite signs. The difference in corresponding patterns 101 and 102 in FIG. 1 is even better visible in representation of the DWL structure by continuous lines 201 as shown in FIG. 2A. DWLs of different signs correspond to the right- and left-spiraling patterns in FIG. 2B.

Figure 3:
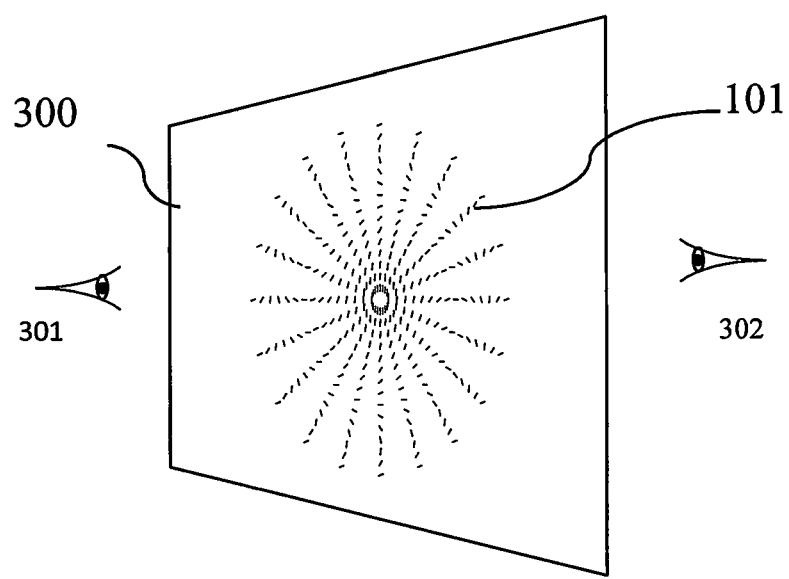
FIG. 3 shows a diffractive waveplate lenses viewed from opposite sides.

In the preferred embodiment of the present invention, DWLs of opposite optical axis modulation signs need not be two separate optical components and is obtained by rotating the DWL around an axis in the plane of the DWL by 180 degrees. The observers 301 and 302 looking at a given DWL from opposite sides in FIG. 3 see patterns of opposite sign.

Figure 4A:
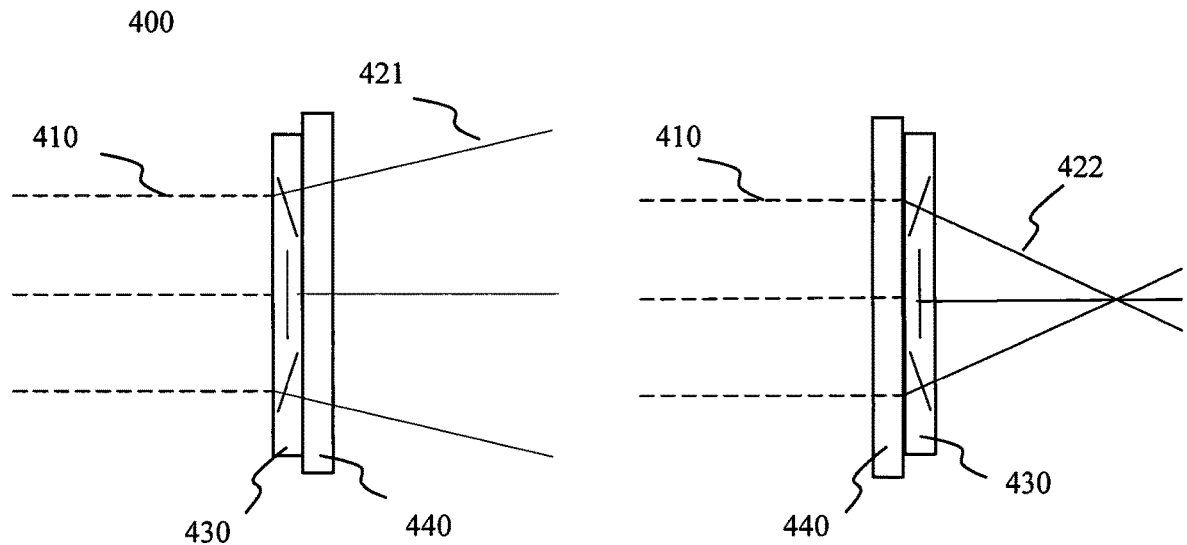
FIG. 4A shows polarization properties of focusing and defocusing of a right-hand circular polarized beam by a diffractive waveplate lens, respectively.
Figure 4B:
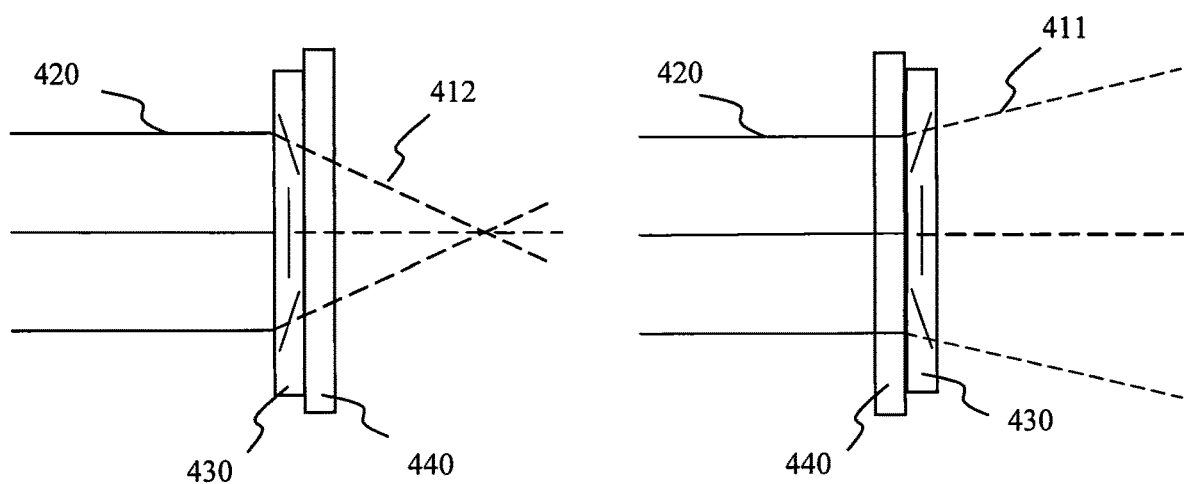
FIG. 4B shows polarization properties of focusing and defocusing a left-hand circular polarized beam by a diffractive waveplate lens, respectively.

This optical asymmetry is described in detail in FIG. 4 wherein the DWL layer 430 is shown on a substrate 440. As an example, a right-hand circular polarized (RHCP) light beam 410 is transformed into a defocused left-hand circular polarized (LHCP) beam 421 when incident from the side of the substrate. Arranging the component 400 with the substrate facing the incident RHCP beam results in a focused LHCP beam 422.

For a LHCP light beam 420 in FIG. 4, the situation is reversed. The LHCP beam 420 is transformed into a focused RHCP beam 412 when incident from the side of the DWL and it is transformed into defocused RHCP beam 411 when incident from the side of the substrate.

Figure 5A:
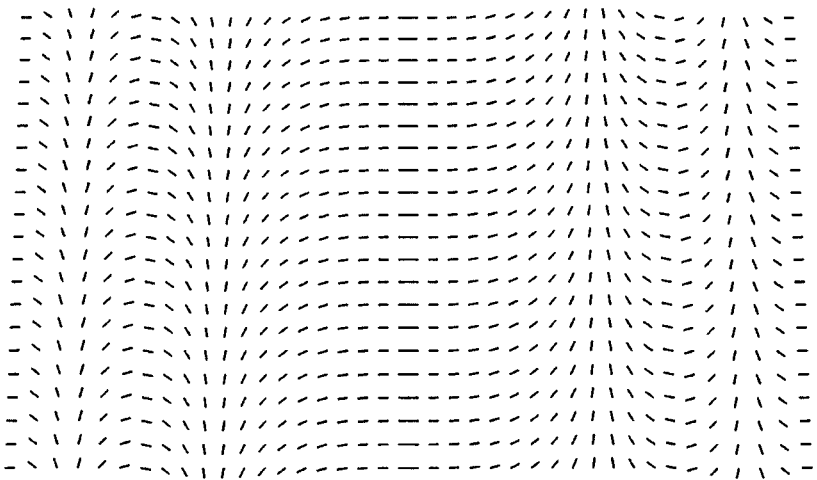
FIG. 5A shows the structure of a cylindrical diffractive waveplate lens of one handedness.
Figure 5B:
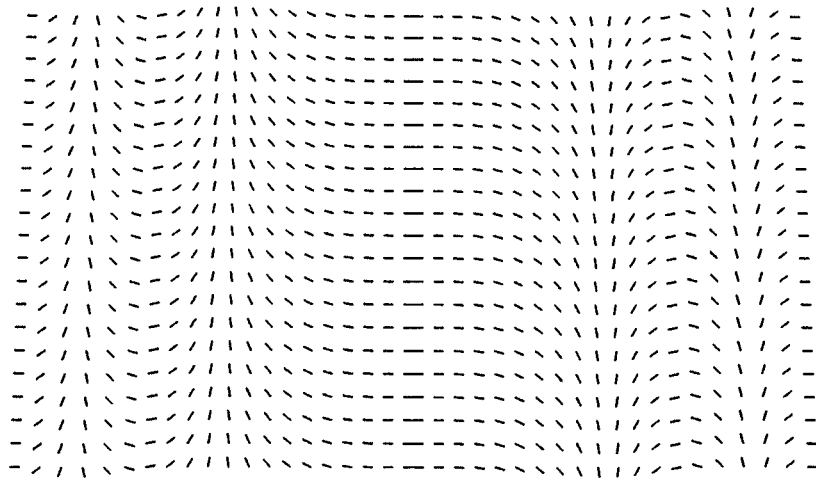
FIG. 5B shows the structure of a cylindrical diffractive waveplate lens of opposite handedness.

In the second type of diffractive waveplate lenses to which the present invention applies, illustrated in FIG. 5, the orientation of the optical axis of the birefringent material comprising the thin film layer depends only on the linear distance x from a central axis. This type of cylindrical diffractive waveplate lens is used for applications such as focusing a beam of light to a line for imaging light from the sun onto a line of photovoltaic devices. In the paraxial approximation, the angle ☐ that the optical axis of the birefringent material makes with the coordinate axis is given by the following equation:

$$\alpha = \pm \frac{k_0}{4f} r^2$$

where $k_0$ and f have the same meanings as before, and x is the distance from the center of the coordinate axis. FIGS. 5A and B correspond to patterns of different sign (cylindrical lenses of different sign).

Figure 6A:
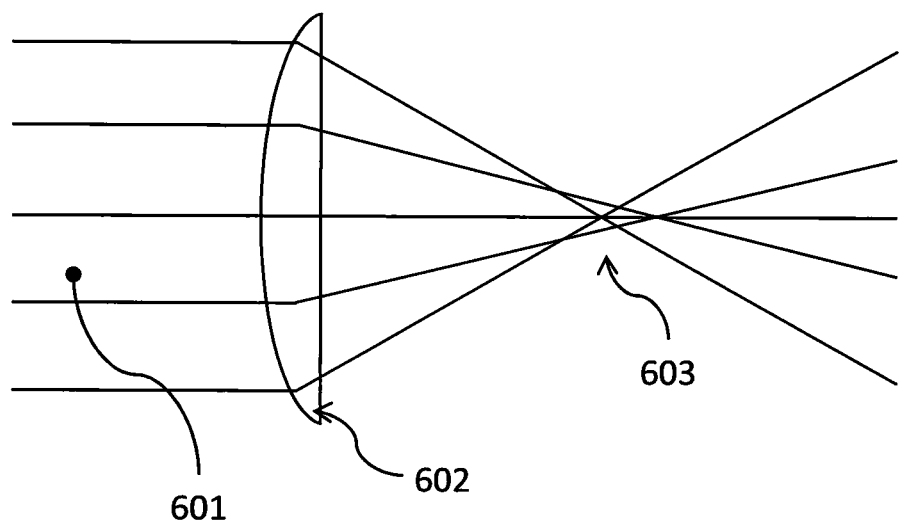
FIG. 6A shows a lens with spherical aberration focusing light to a large focal spot.
Figure 6B:
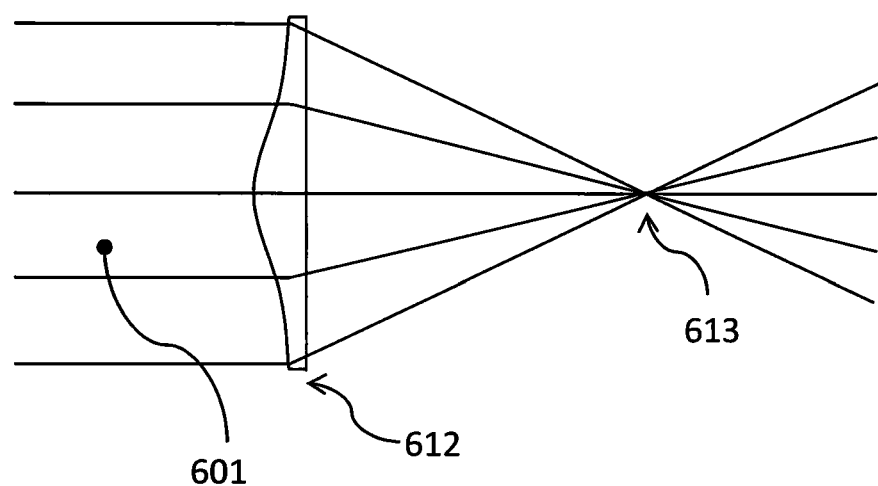
FIG. 6B shows a lens, with spherical aberration corrected, focusing light to a small focal spot.

One of the problems with conventional lenses is spherical aberration, illustrated in FIG. 6A and FIG. 6B, in which an incident collimated beam 601 is focused by a lens 602.

When a refractive material such as glass formed such that one or both surfaces closely approximates a section of a sphere, such as the lens 602, then the resulting structure can be used to focus light as illustrated in FIG. 6A. However, as is well known in the art, when focused by a lens constructed in this way, the rays of light from a distant source are not all brought to the same focal point. Specifically, such a lens with spherical surfaces will bring the peripheral rays, the rays at the edge of the beam, to a focus closer to the lens than the point to which the lens brings the rays closer to the axis. Hence, the rays in the focal region 603 in FIG. 6A do not all pass through the same point. This phenomenon is called spherical aberration.

By means of modifying one of the surfaces of a lens such that the surface is not spherical (i.e. such that the surface is aspherical), all incident light in a collimated beam can be brought to the same focal point, as indicated in FIG. 6B. With an appropriately designed aspheric lens 612, all the rays in the focal region 613 pass through the same point.

However, fabrication of such aspheric lenses is often very expensive, and therefore their use is impractical for many applications.

A major advantage of diffractive waveplate lenses is that the focusing effect of aspheric surfaces of arbitrary form can be produced simply by changing the dependence of optical axis orientation of the birefringent film with coordinate $\alpha = ax + bx^2 + cx^2 + \ldots$. For such lenses, unlike the situation with conventional lenses, the manufacturing expense of a lens that has no spherical aberration will not be significantly greater than for a lens that does have spherical aberration.

Figure 6C:
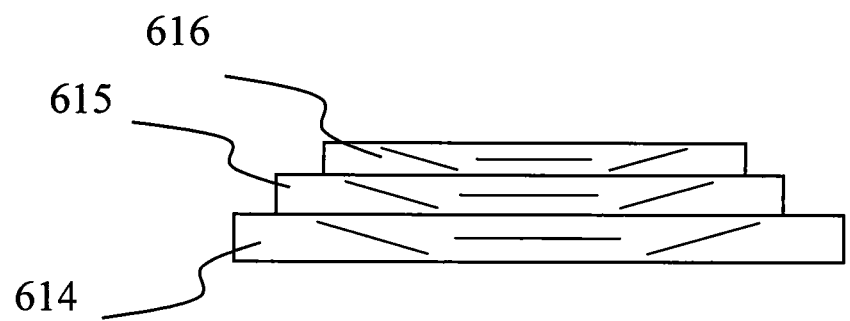
FIG. 6C shows a multilayer system of diffractive waveplate lenses of varying spatial frequency of optical axis orientation and different area.
Figure 6D:
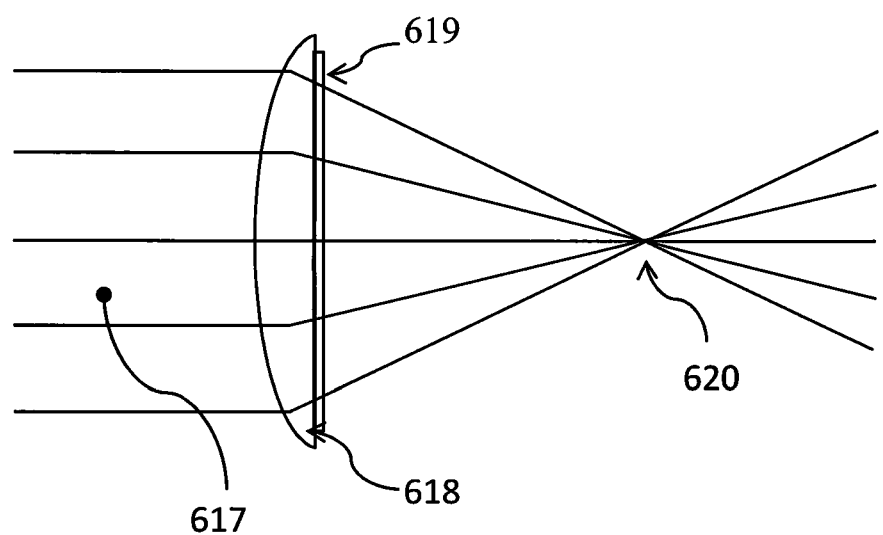
FIG. 6D shows a lens with aberrations corrected with a diffractive waveplate coating.

Another technique for obtaining nonlinear orientation modulation pattern comprises stacking layers of diffractive waveplate lenses with varying modulation patterns and varying degree of overlap. A system of three such layers, 614, 615, and 616 is shown in FIG. 6C.

In one of the embodiments shown in FIG. 60, the thin film diffractive waveplate lens 619 may be deposited on a conventional lens 618 to correct for aberrations and focus an incoming beam 617 onto the same point in space 620.

In general, the optical deflection angle resulting from a light beam propagating through a diffractive waveplate lens depends on the circular polarization of the light. As a result, if the focal length of a lens such as the ones illustrated in FIG. 1 is f for right-hand-circular polarized (RHCP) light as an example, then the focal length of the same lens for left-hand-circular polarized (LHCP) light will be −f. Therefore, a diffractive waveplate lens that converges a collimated beam of RHCP light will diverge a beam of LHCP light. This is illustrated by the action of the diffractive waveplate lens 711 in FIG. 7, in which an incident collimated beam 701, centered on axis 702, and including both a RHCP component and a LHCP component, converges the RHCP component 703 and diverges the LHCP component 704 of the incident beam.

In many applications, one of the functions of the optical system is to bring light to a focal point (in the case of an axially symmetric system) or to a focal line (in the case of a cylindrically symmetric system). It is often desirable for light of all polarizations to be brought to the same focal point or focal line. In the case of diffractive waveplate lenses, for which the focal length of a single lens for LHCP light is opposite in sign to the focal length for the same lens for RHCP light, it is possible to bring light of both polarizations to the same focal point or focal line by the use of two diffractive waveplate lenses. In the preferred embodiment the focal lengths of the two lenses are related as $$|f_2| = |f_1| - \frac{d^2}{|f_1|}$$

where the distance between the two lenses d is smaller than the absolute value of the focal length of the 1$^{st}$ lens, d<|f$_1$|. By that, the back focal length $f_{BFL}$ of the system of two lenses, the distance of the focal spot from the second lens, is determined by equation $$f_{BFL} = \frac{f_1^2}{d} - d$$

Figure 7:
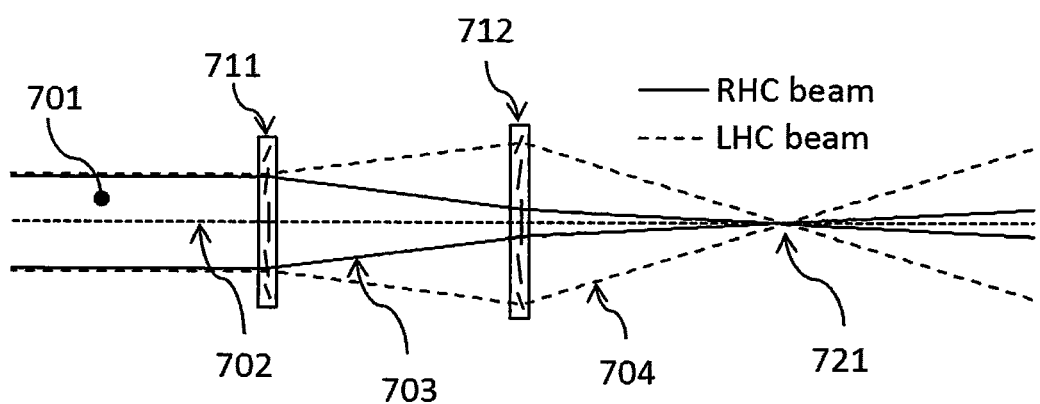
FIG. 7 shows a pair of diffractive waveplate lenses focusing light to the same spot for right hand circular (RHC) polarization as well as left hand circular (LHC) polarization.

For example, the distance between diffractive waveplate lens 711 and diffractive waveplate lens 712 can be 50 mm, the focal lengths of lenses 711 and 712 for RHCP light 703 can be 70.7 mm and −35.4 mm, respectively. Therefore, the focal lengths of lenses 711 and 712 for LHCP light 704 are −70.7 mm and 35.4 mm, respectively. As shown in FIG. 7, this combination of focal lengths and spacings results in both RHCP light 703 and LHCP light 704 being brought to the same focal point 721.

As will be evident to those skilled in the art, if an optical system brings light of both RHCP and LHC polarization to a single point or line focus, then it will bring light of any polarization to the same point or line focus. Therefore FIG. 7 demonstrates the ability with two diffractive waveplate lenses to bring light in any polarized or unpolarized beam to the same point or line focus.

As previously noted, for diffractive waveplate lenses of the type that is the subject of the present invention, the sign of focal length for LHC polarized light is opposite to that of the focal length for RHC polarized light. It was shown by means of FIG. 7 and the associated discussion that despite the difference in focal length for light of the two possible circular polarizations, it is possible to focus light of any polarization with a combination of two diffractive waveplate lenses. However, there may be some applications that an alternative method may be used to focus light of both polarizations, using only a single diffractive waveplate lens and an additional optical element. For example, instead of using two diffractive waveplate lenses, a single diffractive waveplate lens combined with a waveplate and a refractive lens made from a birefringent material could also be used to perform focusing of light of any polarization. Methods of combining diffractive waveplate lenses into optical systems that include such waveplates and birefringent refractive elements will be evident to anyone skilled in the art of optical design, once the fundamental characteristics of diffractive waveplate lenses of this invention are revealed.

Figure 8:
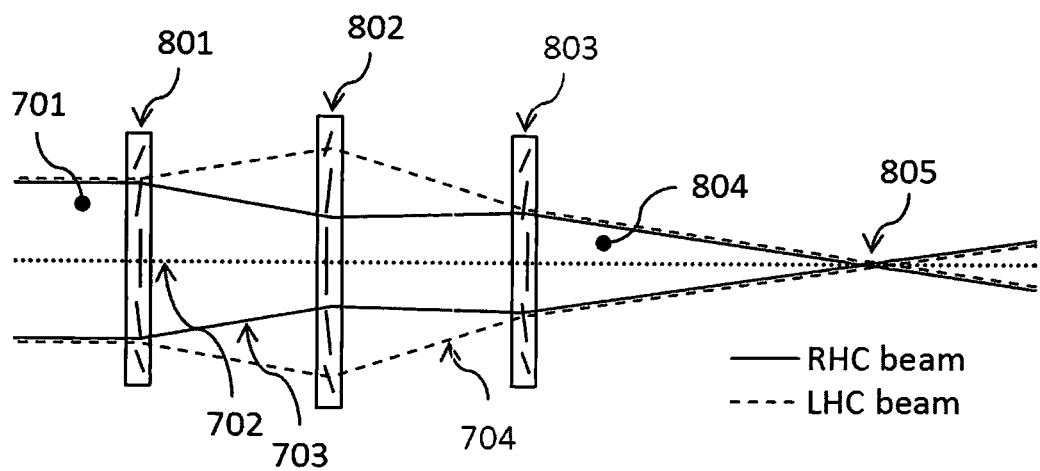
FIG. 8 shows a system of a triplet of diffractive waveplate lenses focusing light to the same spot for light of RHC polarization or LHC polarization, said system having the same effective focal length for either polarization.

As will be evident to those skilled in the art, the effective focal length (EFL) of the optical system comprising lens 711 and 712 in FIG. 7 is much different for light of RHC polarization than it is for light of LHC polarization. In some applications, it is required that light of all polarizations be focused with the same EFL. The capability of a combination of three diffractive waveplate lenses to not only bring light of any polarization to the same point or line focus, but also to have the same EFL for light of any polarization, is illustrated in FIG. 8. As in FIG. 7, in FIG. 8 an incident beam 701 symmetrically disposed about a system optical axis 702, comprising both a RHCP component 703 and a LHCP component 704, is incident on the optical system. However, in FIG. 8, the optical system now consists of three lenses 801, 802, and 803, with a spacing of 30 mm between adjacent lenses, and with focal lengths of 70.7 mm, −35.4 mm, and 45.5 mm, respectively. As shown in FIG. 8, this combination of three diffractive waveplate lenses brings both the RHCP component 703 and the LHCP component 704 of the incident beam to the same focal point 805. While in both FIG. 7 and FIG. 8 both polarization components of the incident light beam 701 are brought to the same focal point, the significant difference between the two figures is that in FIG. 8, the cone angle of the cone of light 804 that converges to the focus 805 is the same for both the RHC component 703 and the LHC component 304, as must be the case if and only the system EFL is the same for both components. FIG. 8 therefore demonstrates that with three diffractive waveplate lenses, light of any polarization can be brought to the same focal point, with the same EFL.

Due to the diffractive nature of diffractive waveplate lenses, the deflection angle for a given grating is a function of wavelength, in accordance with the well-known transmission grating diffraction condition, $d \sin \theta = m\lambda$. Here d is the grating spacing, $\theta$ is the angle through which the grating deflects the beam, m is the order of diffraction, and $\lambda$ is the wavelength. The phase gratings used in diffractive waveplate lenses are designed to be continuous in nature, eliminating all but the first orders of diffraction. Also, for illustrative purposes, it is useful to consider only the paraxial case, in which the angle through which the beam is diffracted is small compared with $\pi$, in which case sin can be approximated by $\theta$. The equation above therefore becomes $d\theta \approx \lambda$. That is, in the paraxial approximation, the deflection angle of a ray of light incident on a local area of a diffractive waveplate lens is directly proportional to the wavelength of the light. As a direct consequence, the focal length of the lens is inversely proportional to wavelength.

Because of this strong dependence of the focal length of a diffractive waveplate lens on wavelength, such lenses may be used to correct for chromatic aberration in optical systems containing refractive elements. Chromatic aberration, as the expression is used here, is the dependence of the focal position on wavelength. Due to the dependence of the index of refraction n of any dielectric medium on wavelength, every imaging system that employs such media suffers from chromatic aberration.

Figure 9A:
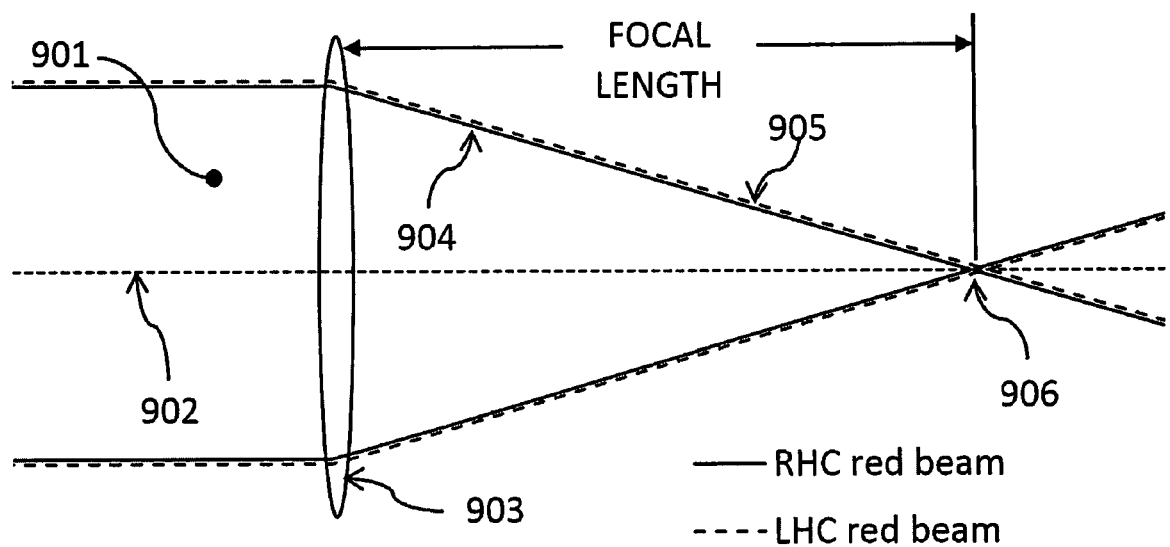
FIG. 9A shows a conventional glass lens focusing light in the red region of the spectrum to a small focal spot.

To illustrate the ability of diffractive waveplate lenses to correct for chromatic aberration, a specific example will be used. FIG. 9A illustrates an imaging system employing a single refractive element made with BK7 glass, an optical material available from Schott Advanced Optics. A collimated beam 901 of white light from a distant source is incident on spherical lens 903 with aperture centered on axis 902. Although BK7 is isotropic, and therefore does not act any differently on RHCP light than it acts on LHCP light, we will distinguish between these two components of the incident unpolarized light because later in this discussion, diffractive waveplate lenses will be considered whose effects differ between these two polarization components. With only the refractive element made from BK7 in place, both the RHCP component 904 and the LHCP component 905 of the red component of the white input beam are brought to the same focal point 906.

Figure 9B:
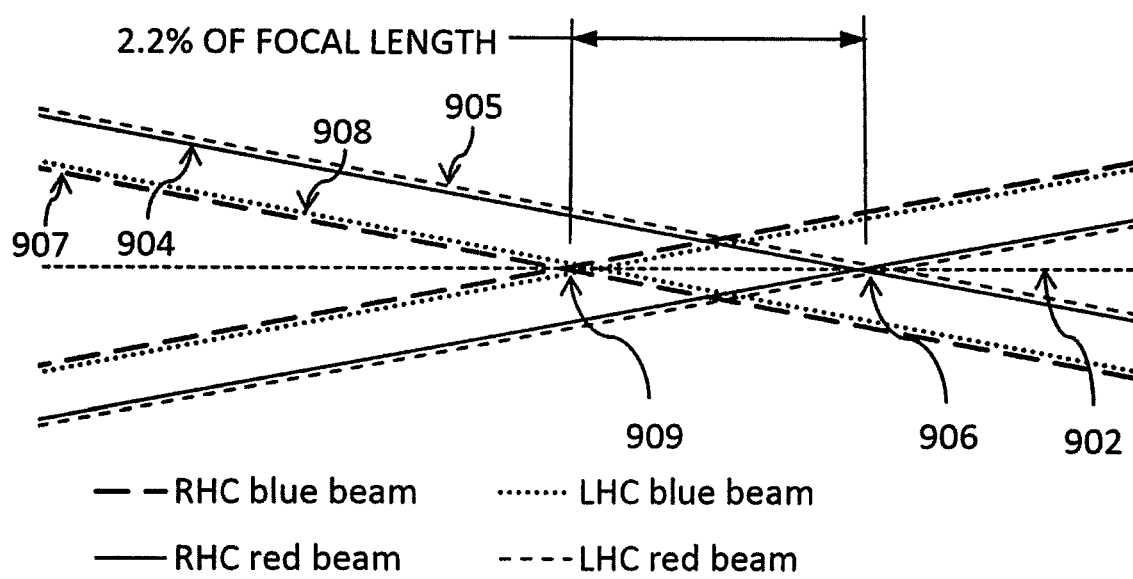
FIG. 9B shows the paths of rays of light in the red region of the spectrum, and light in the blue region of the spectrum, near the focus of a glass lens, illustrating the fact that light with different wavelengths is focused to different axial locations by the glass lens.

The BK7 material from which the refractive lens in FIG. 9A is made has an index of refraction of n=1.515 for red light (wavelength $\lambda$=650 nm) and n=1.526 for blue light (wavelength $\lambda$=450 nm). As a result, the focal length of the lens is slightly shorter for blue light than it is for red light. This is shown in FIG. 9B, showing a magnified view of the region near the focal point. The focal point 909 on the axis 902 of the input beam, for both the RHCP component of the blue light 907 and the LHCP component of the blue light 908, is 2.2% closer to the lens than the focal point 906 for the two polarization components of the red light.

For optical systems such as cameras, it is undesirable for the focal positions at any two wavelengths within the operating wavelength band to differ significantly. Therefore, chromatic aberration correction is an important part of the design of such optical systems. The most common approach to chromatic aberration correction refractive imaging systems is to include refractive elements of multiple types, with various indices of refraction and various dependences of index of refraction on wavelength. These approaches increase the complexity and cost of the system. Therefore, there is a need for alternative approach to chromatic aberration correction.

Figure 10A:
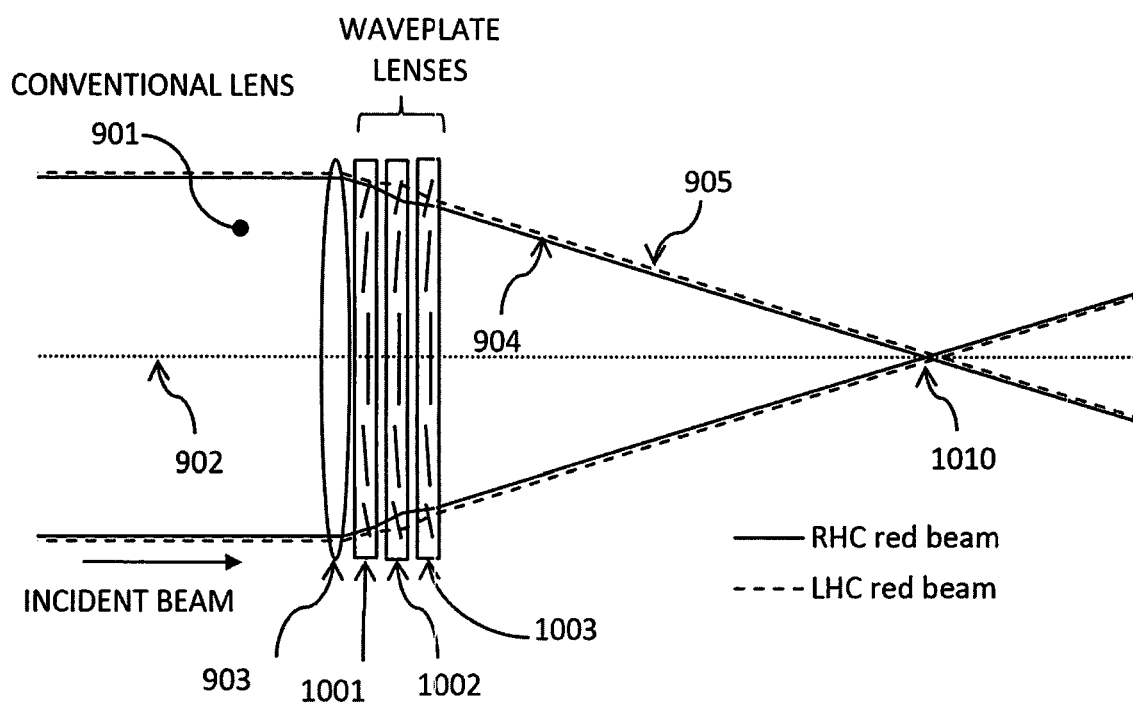
FIG. 10A shows a combination of one glass lens and three diffractive waveplate lenses focusing light in the red region of the spectrum to a small focal spot.

FIG. 10A illustrates correction of the chromatic aberration in a conventional refractive lens by employment of a set of three diffractive waveplate lenses. As was the case for FIGS. 9A and 9B, white light collimated beam 901 is incident along an axis 902 onto the conventional BK7 glass lens 903. FIG. 10A includes three diffractive waveplate lenses 1001, 1002, and 1003. As is evident from the figure, the path of red light through the combined system is slightly different for the RHCP component 904 than it is for the LHCP component 905, but both of the polarization components of the red light are brought to the same focal point 1010. The focal lengths of the lenses shown in the figure for RHCP polarized red light are 10.00 mm, 14.00 mm, −7.00 mm, and 14.07 mm for lenses 903, 1001, 1002, and 1003, respectively. As noted previously, for the diffractive waveplate lenses, the focal lengths change sign for LHC polarized light.

Figure 10B:
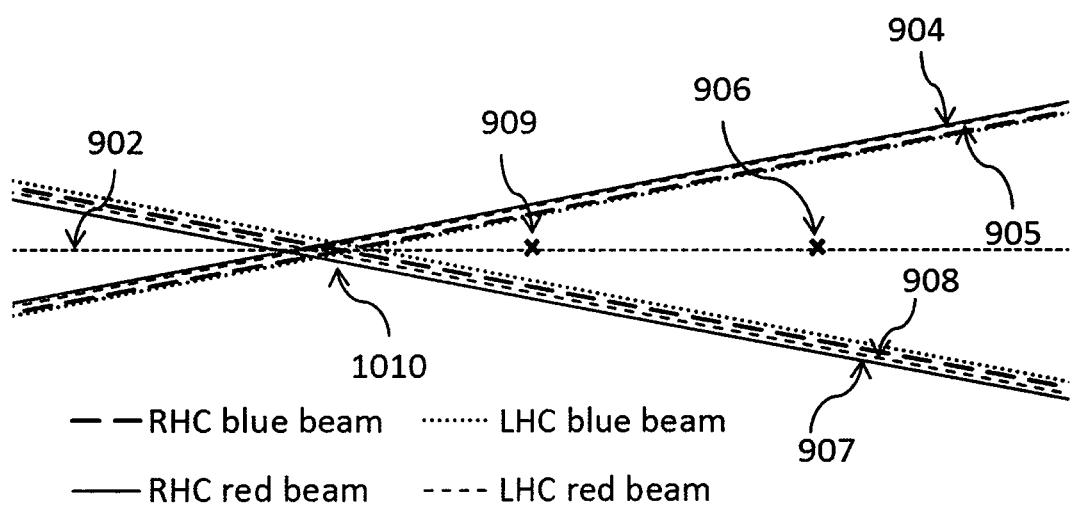
FIG. 10B shows the paths of rays of light in the red region of the spectrum, and light in the blue region of the spectrum, near the focus of the combination of one glass lens and three diffractive waveplate lenses, illustrating the fact that light with different wavelengths is focused to the same axial location by said combination of lenses.

FIG. 10B shows the ability of the lens combination illustrated in FIG. 10A to correct for chromatic aberration. The focal positions 906 and 909 for red and blue light, respectively, before the addition of diffractive waveplate lenses 1001, 1002, and 1003, are shown in FIG. 10B for reference. Light of all four considered polarization/wavelength combinations is brought to the same focal point 1010 after the addition of lenses 1001, 1002, and 1003. In FIG. 10B, the paths of the RHC red beam 904, LHC red beam 905, RHC blue beam 907, and LHC blue beam 908 are shown slightly offset vertically for clarity, but for the considered optical design, the four beams come to exactly the same focal point 1010.

In the discussion of FIG. 6 it was noted that by adjusting the grating spacing in a diffractive waveplate lens, spherical aberration can be eliminated. In the discussion of FIG. 10 it was demonstrated that chromatic aberration correction of a refractive imaging system is possible by the addition of appropriate diffractive waveplate lenses. Once the mechanism of correcting for spherical aberration alone, and the mechanism for correcting for chromatic aberration alone, methods will be evident to those skilled in the art that allow the use of diffractive waveplate lenses to be used to simultaneously compensate for both spherical and chromatic aberration.

Switchable Lens

Figure 11A:
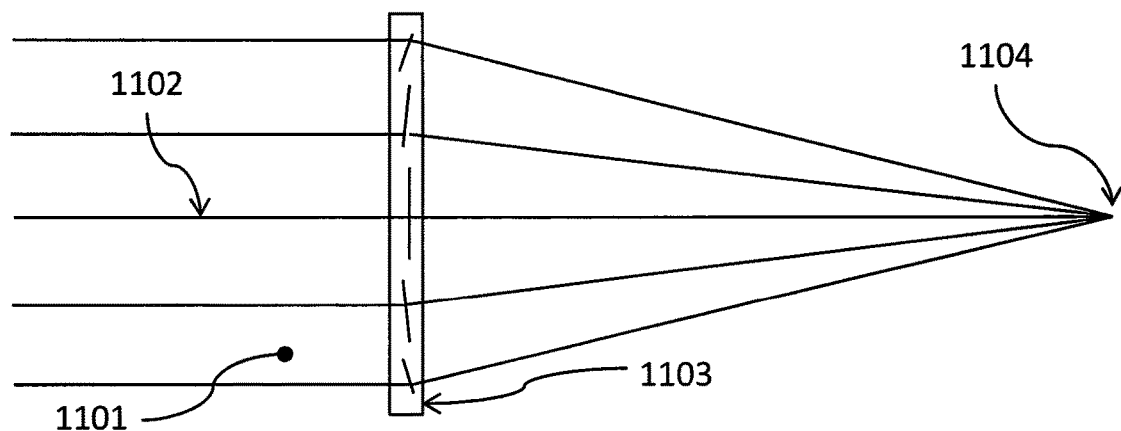
FIG. 11A shows the focusing of a collimated beam of light by an electrically switchable diffractive waveplate lens, with the lens in the active state (electric field off).
Figure 11B:
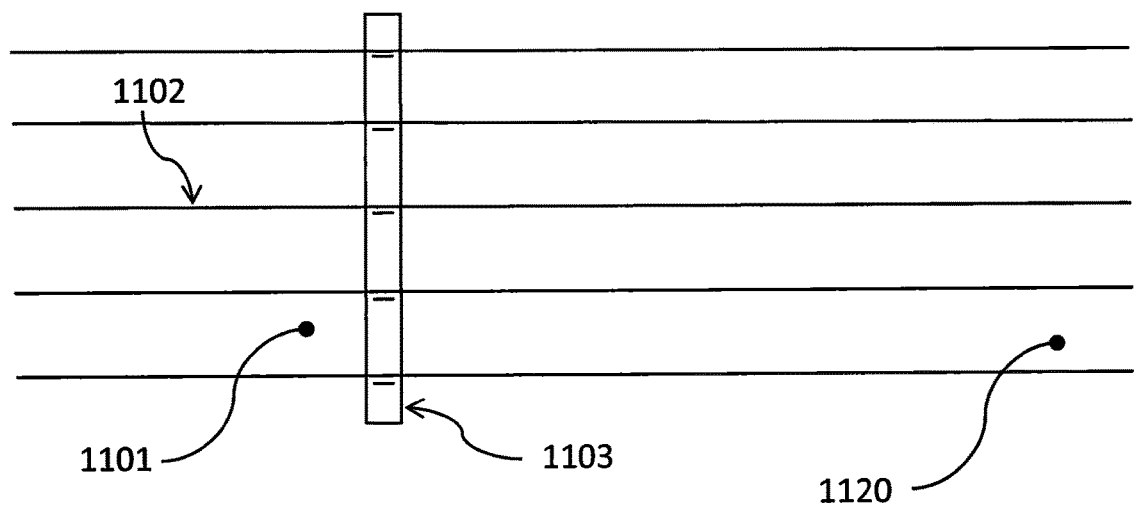
FIG. 11B shows the lack of focusing of a collimated beam of light by an electrically switchable diffractive waveplate lens, with the lens in the passive state (electric field on).

It is well known that the optical properties of liquid crystal based devices can be made to be controllable by means of an electric field across the medium containing the liquid crystal material. A common example of this is the LCD (liquid crystal display) used in computer monitors and television displays. Diffractive waveplate lenses can be constructed such that the focusing properties can be turned on and off by means of the application of an electric potential across the device. An example of such a device is illustrated in FIG. 11. In FIG. 11A, with no electric field applied, an incident collimated beam 1101 enters a diffractive waveplate lens 1103 centered on axis 1102 of the optical system, and is focused by the lens to focal point 1104. In FIG. 11B, due to the effect of an applied electric field, the orientation of the liquid crystal molecules in lens 1103 is changed in such a way that the beam is no longer focused by the lens, and the output beam 1120 remains collimated.

1. Electrically Tunable Focusing System

Electrically Tunable Focusing System

Figure 12A:
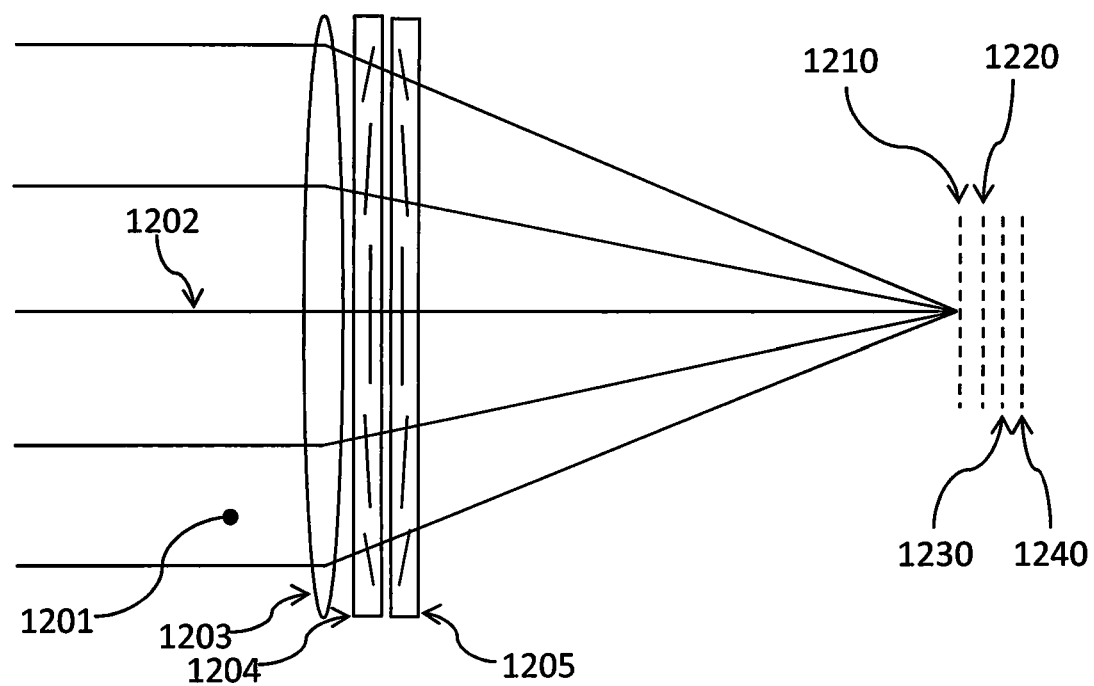
FIG. 12A shows the focusing of a collimated beam of light by a combination of a conventional refractive lens and two electrically switchable lenses, with both diffractive waveplate lenses in the active state (electric field off).
Figure 12B:
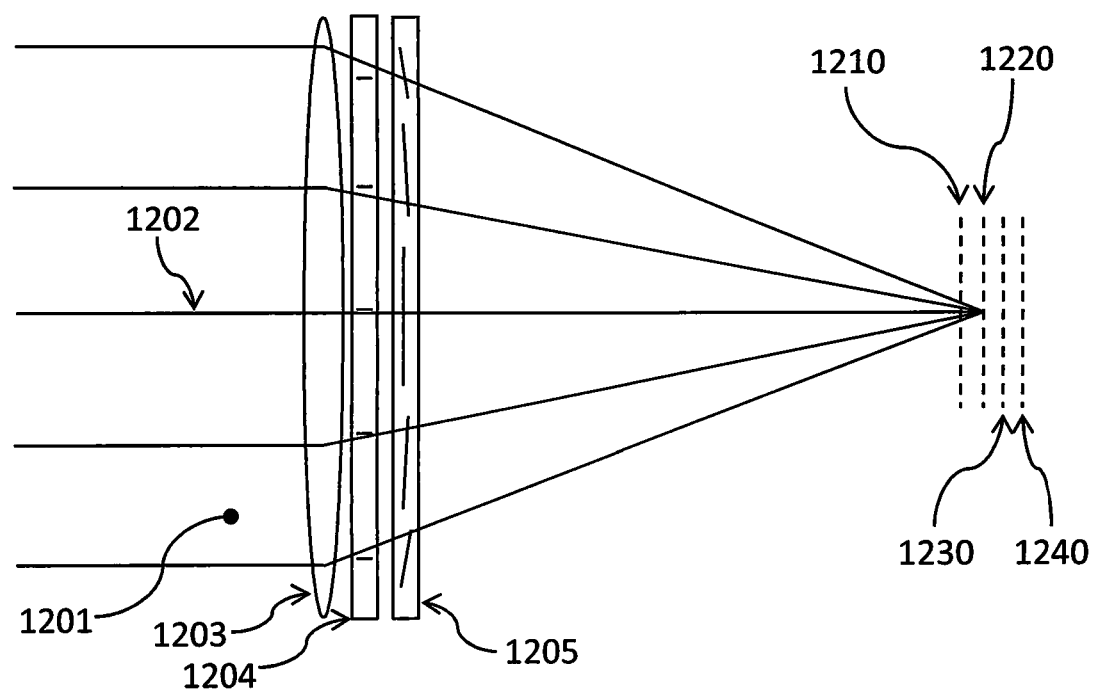
FIG. 12B shows the focusing of a collimated beam of light by a combination of a conventional refractive lens and two electrically switchable lenses, with the first diffractive waveplate lens in the passive state (electric field on), and the second diffractive waveplate lens in the active state (electric field off).
Figure 12C:
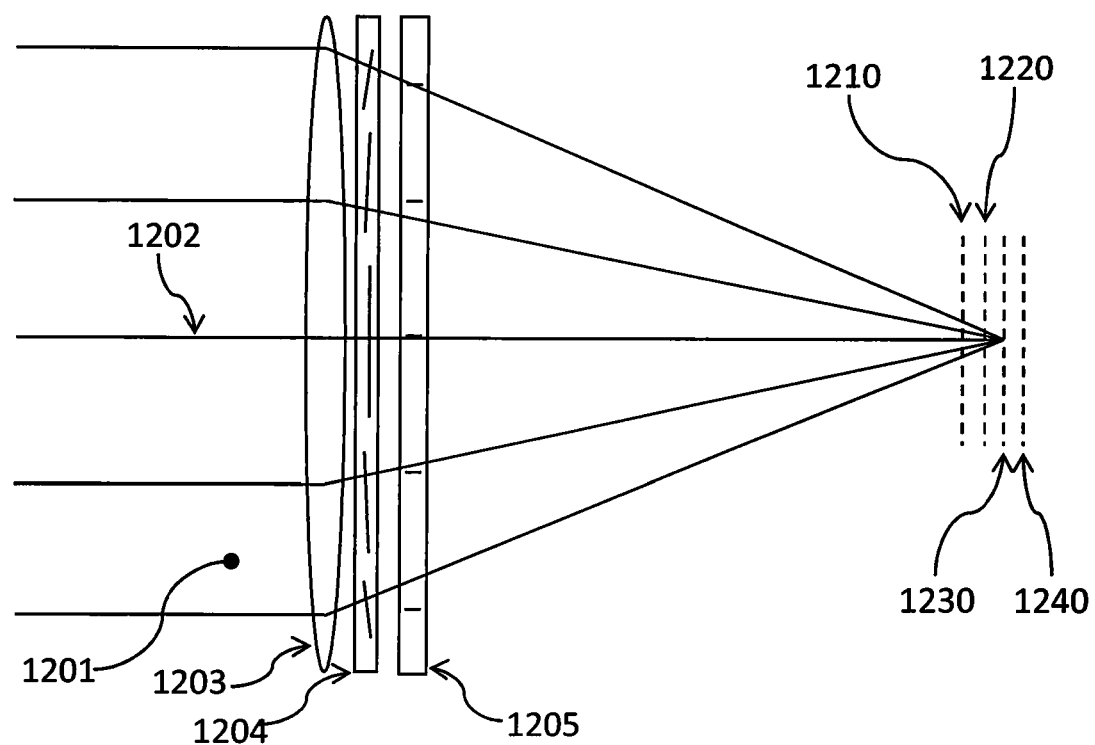
FIG. 12C shows the focusing of a collimated beam of light by a combination of a conventional refractive lens and two electrically switchable lenses, with the second diffractive waveplate lens in the passive state (electric field on), and the first diffractive waveplate lens in the active state (electric field off).
Figure 12D:
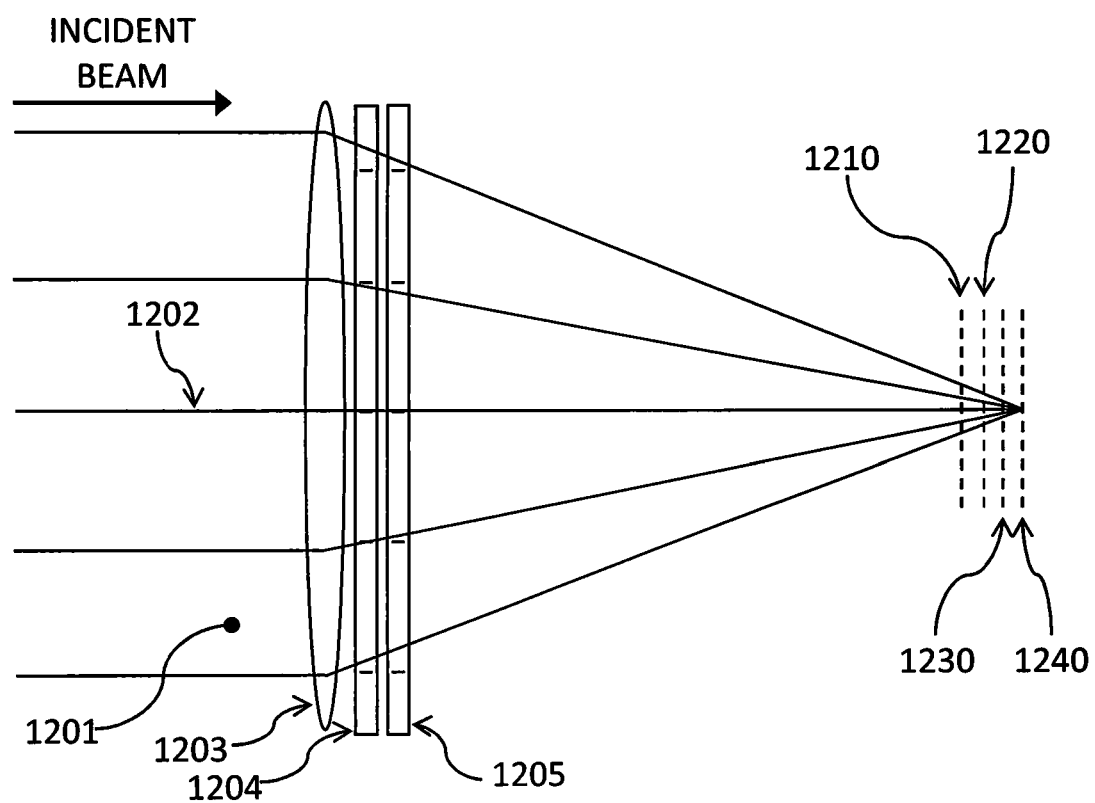
FIG. 12D shows the focusing of a collimated beam of light by a combination of a conventional refractive lens and two electrically switchable lenses, with both diffractive waveplate lenses in the passive state (electric field on).

One of the potential applications of such switchable diffractive waveplate lenses is to provide a purely electronic means of focusing for an optical imaging system, without the need to move any optical elements. This would be highly desirable in some applications because it eliminates the cost, weight, and reliability issues of mechanical actuators in the focusing system. One of the many possible embodiments of such an electronic focusing system wherein a combination of two electrically switchable diffractive waveplate lenses is used to provide four distinct focus positions is illustrated in FIG. 12. FIG. 12A shows the case in which a beam 1201 is incident on the input aperture centered along axis 1202, and is focused to a point in focal plane 1210 by a combination of lenses 1203, 1204, and 1205. In FIG. 12A both of the diffractive waveplate lenses, 1204 and 1205, are turned on so they both pull the focal position towards the lens system FIG. 12B is the same as FIG. 12A except that in FIG. 12B, lens 1205 remains on but lens 1204 has been shut off. This results in the focal point shifting from focal plane 1210 to focal plane 1220. FIG. 12C is also the same as FIG. 12A except that in FIG. 12C, lens 1204 remains on but lens 1205 has been shut off. This results in the focal point shifting from focal plane 1210 to focal plane 1230. FIG. 12D is also the same as FIG. 12A except that in FIG. 12D, both lens 1204 and lens 1205 have been shut off. This results in the focal point shifting from focal plane 1210 to focal plane 1240.

In the design concept illustrated in FIG. 12A, four different focal positions are accessible by means of switching two lenses on and off. This is accomplished by using diffractive waveplate lenses of different focal power. By this means, in general, with k switchable lenses, $2^k$ distinct focus positions can be made accessible, particularly, equally spaced. Each lens may have twice the focal power of the previous one, for example.

Camera Lens

An example of uses of electrically switchable diffractive waveplate lenses of the present invention are camera lenses and machine vision wherein the contrast reduction due to presence of defocused beam does not affect required image information obtained due to focused portion of the beam, Fiber Illuminator/Focusing Switching System An important use of diffractive waveplate lenses in the current invention are polarization maintaining fibers. As an example, the diffractive waveplate lens coated at the output facet of the fiber may allow collimating or focusing the light emerging from the fiber. Thus, changing the state of polarization of a laser light injected into a fiber would allow, for example, switching the light at its output between illuminating state used for imaging and focused state that may be used for example, for surgery.

Fiber Coupler

The capability to switch a diffractive waveplate lens from an active to a passive state makes possible many other applications in which optical beams are manipulated by a switchable lens. One of these many applications is the switching on and off of optical coupling between the output from one optical fiber and the input of another optical fiber.

Figure 13A:
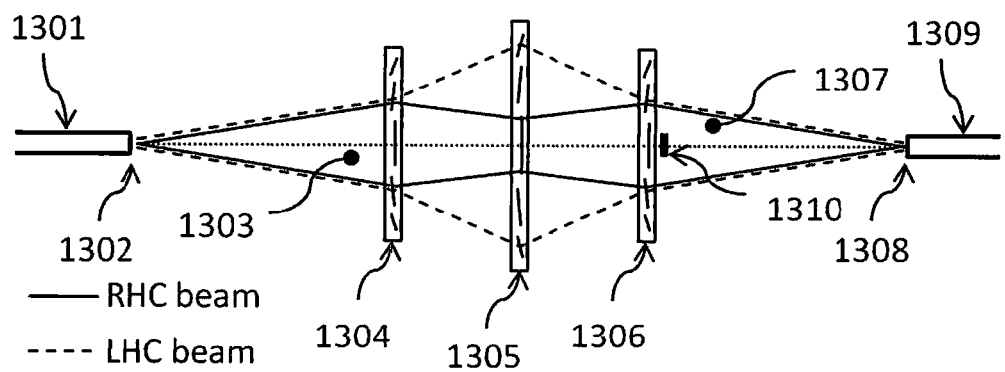
FIG. 13A shows the focusing of the output of an optical fiber into the input of another optical fiber by means of a combination of three electrically switchable diffractive waveplate lenses, with all three lenses in the active state (electric field off).
Figure 13B:
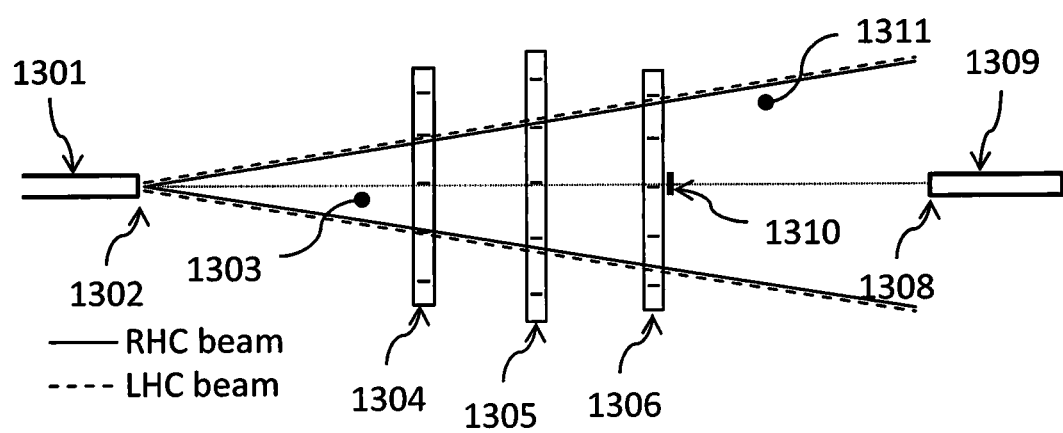
FIG. 13B shows the absence of focusing of the output of an optical fiber into the input of another optical fiber by means of a combination of three electrically switchable diffractive waveplate lenses, with all three lenses in the passive state (electric field on).

Such optical switching is illustrated in FIG. 13A and FIG. 13B. In FIG. 13A, light from the tip 1302 of optical fiber 1301 expands away from the tip within a light cone 1303 characteristic of the fiber type. This output light is captured and focused by the diffractive waveplate lenses 1304, 1305, and 1306. Except for a small fraction of the light in the converging cone 1307 of the light beam, all the light is focused into the tip 1308 of a second optical fiber 1309. A small fraction of the light is blocked because it impinges on a beam block 1310, but almost all the light goes around the beam block and reaches fiber tip 1308.

As indicated in FIG. 13A, due to the specific arrangement of the diffractive waveplate lenses 1304, 1305, and 1306, light of both RHC and LHC polarization is captured and focused into fiber 1309. As will be evident to those skilled in the art, the fact that both RHC and LHC polarized light is captured and focused into fiber 1309 implies that light of any polarization emanating from fiber tip 1302 will be captured and focused by the lens combination comprised of lenses 1304, 1305, and 1306.

Although a specific exemplary arrangement of the lenses is shown in FIG. 13A, it will be evident to those skilled in the art that it is in general true that by appropriate selection of lens spacing and focal lengths, a combination of three lenses can always be found to couple the radiation from one fiber to another for any spacing between the fiber tips, and for any wavelength. The specific arrangement used as an example in FIG. 13A is for a spacing from fiber tip 1302 to lens 1304 of 1 mm, a spacing between each adjacent pair of lenses of 0.5 mm, a focal length of diffractive waveplate lenses 1304 and 1306 of 0.58 mm for RHC light, and a focal length of diffractive waveplate lens 1305 for RHC light of −0.43 mm.

Switching off the coupling from fiber 1301 to fiber 1302 is accomplished by turning off the three lenses 1304, 1305, and 1306. The resulting optical configuration after the three lenses are switched off is shown in FIG. 13B. The cone of light 1307 that emerges from the combination of lenses is now diverging beam 1311 instead of converging, and no light reaches the input tip 1308 of fiber 1309.

2. Partially Focused Beams

Partially Focused Beams

The transition of diffractive waveplate lenses such as lenses 1304, 1305, and 1306 in FIG. 13A and FIG. 13B from the "on" state (i.e. focusing or defocusing the input beam) to the "off" state (i.e. passing the beam without deflection) can be converted into a continuous process, such that an arbitrary and selectable fraction of the optical power in the beam can be deflected by the diffractive structure of the diffractive waveplate lens, and the balance of the optical power in the beam can be passed without deflection. This is accomplished by applying an electric potential to the diffractive waveplate lens that results in an optical retardation of one linear polarization relative to the other of more than zero retardation (at which no beam deflection occurs), but less than one-half wave of retardation (at which 100% of the optical power in the beam is deflected by the diffractive structure). By appropriately adjusting the magnitude of the applied electric potential, the fraction of power focused or defocused by the lens can be adjusted to any value between 0% and 100%, For example, in the fiber coupling embodiment shown in FIG. 13A and FIG. 13B, the fraction of the power transferred from fiber 1301 to fiber 1309 can be varied from 0% to nearly 100%. In other words, the gradual transition of the lenses from the state in which they do not deflect the beam at all, to the state in which they deflect 100% of the optical power in the beam, results in a variable optical attenuator.

Figure 13C:
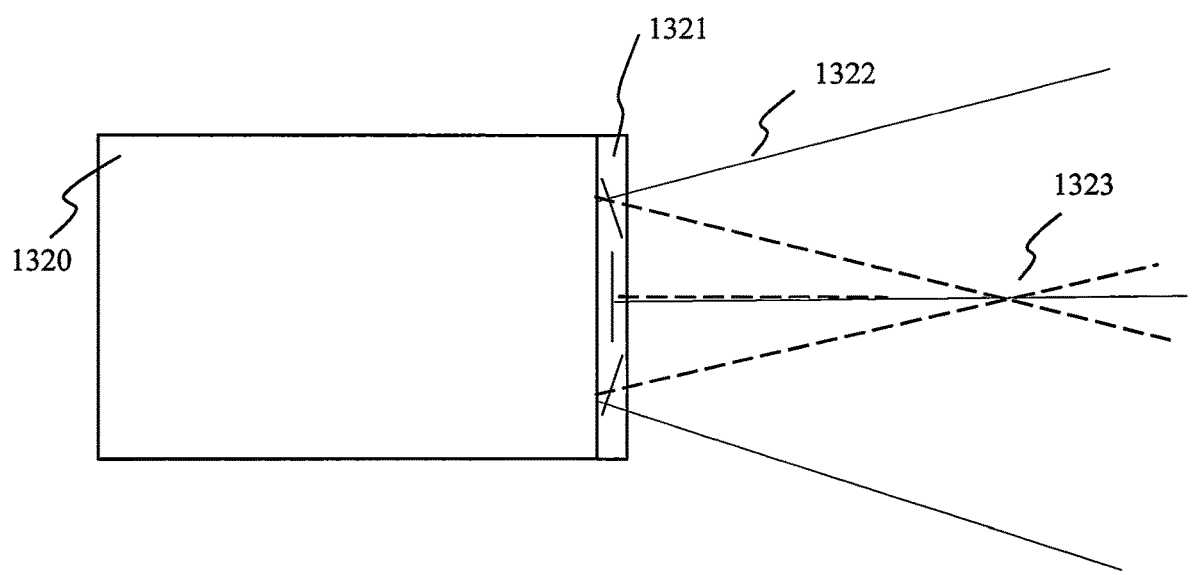
FIG. 13C shows the tip of an optical fiber outputting both focused and defocused beams with the proportion between them being set by a polarization control element at the input of the fiber.

In a preferred embodiment shown in FIG. 13C the diffractive waveplate lens 1321 is coated at the output facet of a fiber 1320 to split the output beam between focused 1323 and defocused 1322 beams controlled by the polarization of light at the input of the fiber.

Switching from Non-Focusing to Focusing State

In one realization of the present invention, the phase retardation of the lens is chosen to fulfil full-wave condition wherein diffraction, hence, focusing action of the lens is absent. Application of an electric field reduces the phase retardation to half-wave condition thus setting in the lensing action. Instead of the electric field, switching can be induced also by temperature, light, and other influences that change either the order parameter or orientation of the liquid crystal diffractive waveplate lens.

In another preferred embodiment, the initial non focusing state is obtained by arrangement of at least two diffractive waveplate lenses. Switching at least one of the lenses in such a system transforms it into a focusing state.

Switching Diffractive Waveplate Lens System by Polarization Modulators

Figure 14A:
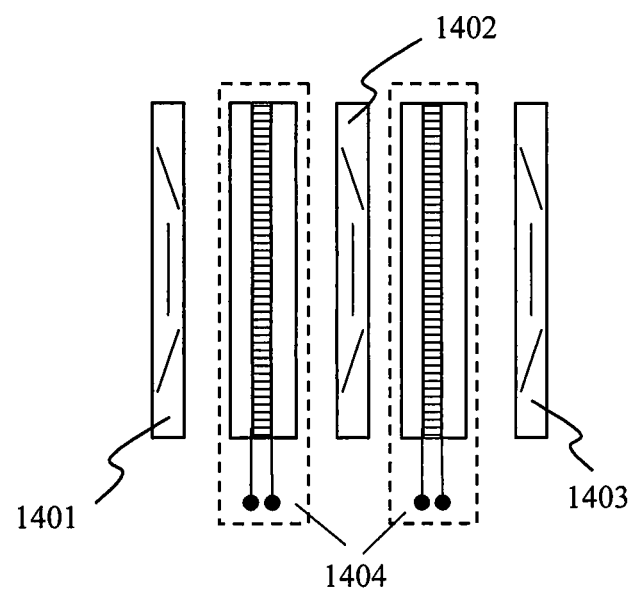
FIG. 14A shows a system of diffractive waveplates interspaced with polarization control elements for switching the focus of the beam to different spots in space.
Figure 14B:
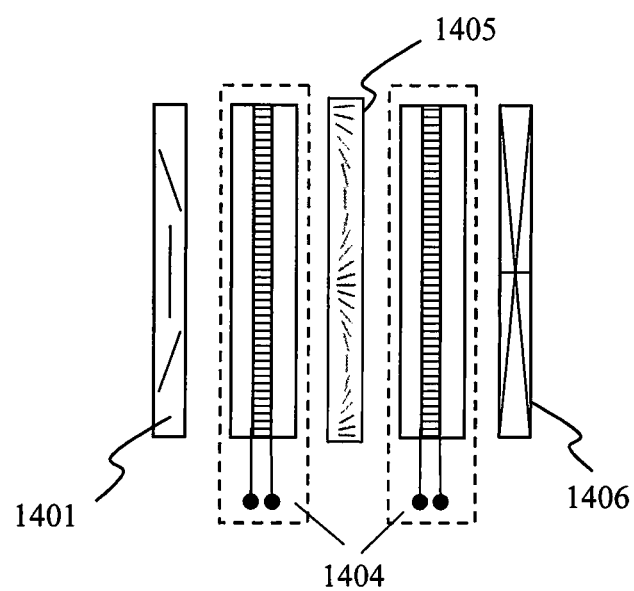
FIG. 14B shows a switchable system comprising variety of diffractive waveplate structures.

As an alternative to switching focusing properties of diffractive waveplate lenses, the focus position of a light beam at the output of a system of diffractive waveplate lenses can be controlled by using variable phase retardation plates to switch the polarization handedness of a beam at the output of diffractive waveplate lenses as shown in FIG. 14. By switching the handedness of polarization, the focusing powers of subsequent lenses, 1401, 1402 and 1403, in the example shown in FIG. 14A, can be added or subtracted from each other focusing an input beam to different points in space. Moreover, diffractive waveplates of different functionalities can be combined in series with polarization switching components 1404. As shown in FIG. 14B, the optical system can combine, for example, a DW lens 1401, a cycloidal diffractive waveplate 1405, and vector vortex waveplates 1406 along with diffractive waveplate lenses, to switch not only focus position, but propagation direction and the phase profile of the beam as well.

Figure 14C:
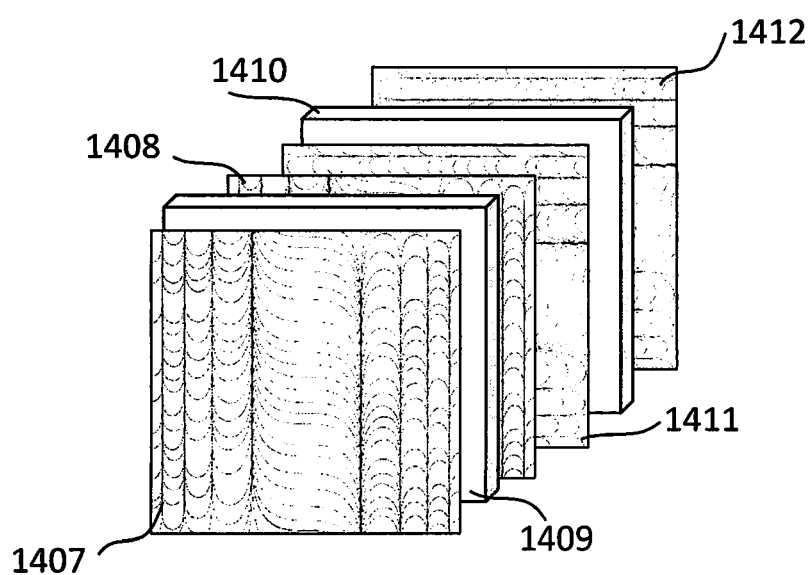
FIG. 14C shows a system for switching the orientation of a light beam intensity distribution with cylindrical diffractive waveplates.

In a preferred embodiment, cylindrical diffractive waveplate lenses can be sequenced with polarization switching components 1404 to obtain a beam of different orientation of ellipticity axis. FIG. 14C shows such an opportunity for a horizontal and vertical alignment of the beam intensity distribution profile obtained when focusing with cylindrical lenses. The cylindrical diffractive waveplate lenses 1407 and 1408 are identical in this embodiment. The cylindrical diffractive waveplate lenses 1411 and 1412 are also identical but aligned perpendicular to the orientation of the lenses 1407 and 1408. Each pair is interspaced with polarization switching components 1409 and 14010, for example a liquid crystal switchable phase retardation layer to generate either undiffracted or diffracted/focused beams.

Figure 15:
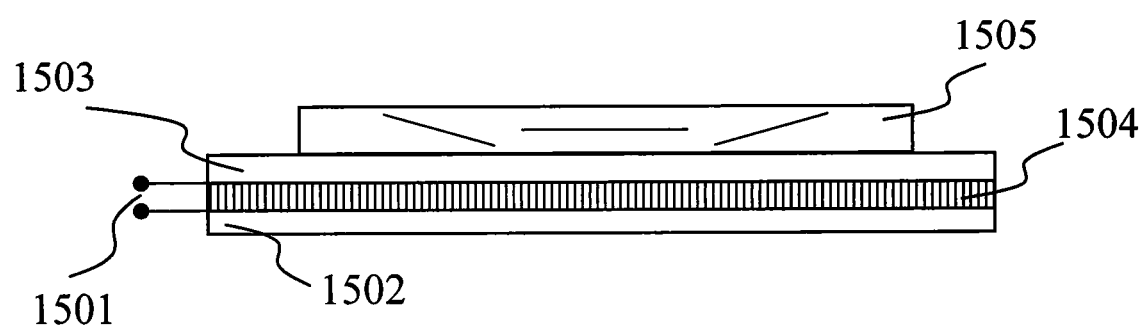
FIG. 15 shows a diffractive waveplate lens deposited on one of the substrates of the switchable phase retarder.

In a preferred embodiment, the switchable phase retarder serves as substrate for the diffractive waveplate film 1505 as shown in FIG. 15. The switchable phase retarder is comprised of substrates 1502 and 1503 with transparent electrodes for application of an electric field 1501, and the electro-optical material in-between 1504 such as a liquid crystal.

Figure 16:
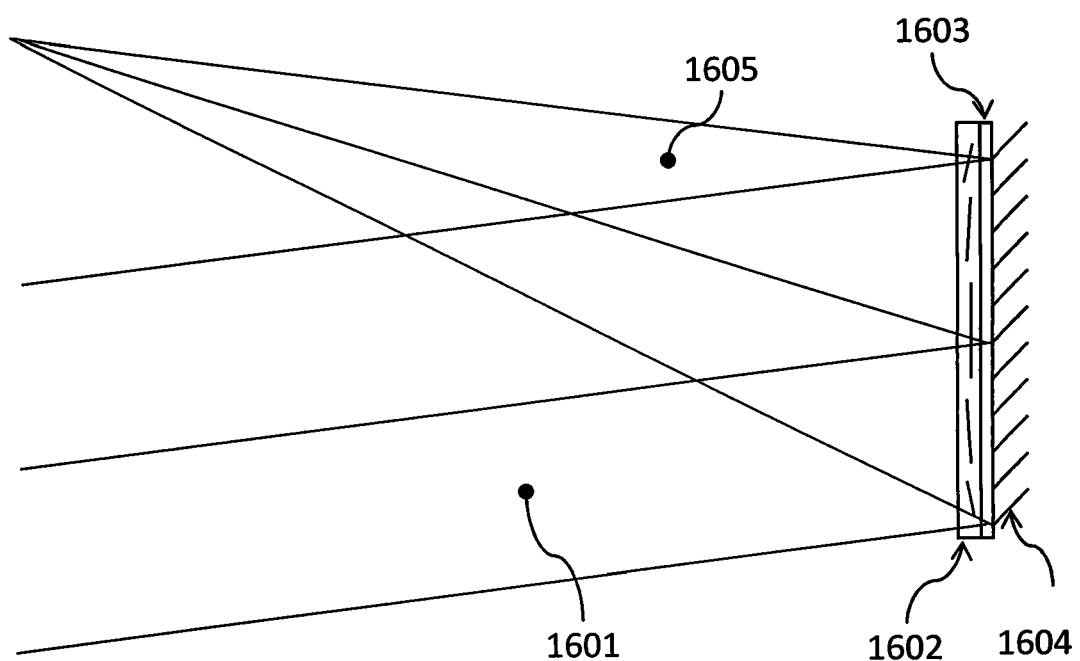
FIG. 16 shows a flat mirror comprising a switchable phase retarder and a diffractive waveplate lens.

While all of the exemplary embodiments discussed herein are of a realization of diffractive waveplate lenses employed in a mode in which the optical beam is transmitted through the thin film diffractive waveplate lens and through the underlying substrate, an alternative embodiment is to apply the thin film diffractive waveplate lens to a flat mirror as demonstrated in FIG. 16. In this manner, flat reflective optical elements can be fabricated to have a wide variety of beam deflecting properties, including the ability to focus light with a flat reflective optical element. In one of the preferred embodiments shown in FIG. 16, a flat mirror 1604 comprises a variable phase retardation film 1603 and a diffractive waveplate lens 1602. A circular polarized collimated light beam 1601 may thus be reflected from the system as a focused beam 1605, for example.

The exemplary embodiments described herein have assumed either explicitly or implicitly that the thin film constituting the diffractive waveplate lens is applied to the flat surface of a solid substrate such as glass. Neither the assumption of a solid substrate, nor the assumption of a flat surface, should be taken as restrictive in defining the potential embodiments of this invention. As will be evident to anyone skilled in the art, the coatings may be applied to curved substrates, and to flexible substrates. All of the exemplary embodiments described herein could also be realized with either a curved substrate, a flexible substrate, or a substrate that is both curved and flexible.

Microwave, Infrared, Ultraviolet, and X-Ray Regions of the Spectrum

By merely changing the thickness of the layer, in a preferred embodiment of current invention, diffractive waveplate lenses are optimized for use in different parts of the spectrum, spanning microwave and to short wavelengths.

While the invention has been described, disclosed, illustrated and shown in various twits of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An optical communication system comprising:
    a laser light source;
    a flat mirror;
    a quarter wave plate deposited on the flat mirror;
    a system of one or more diffractive waveplates with switchable optical power for receiving laser light from the laser light source, said one or more diffractive wave plates are selected from a group consisting of diffractive waveplate lenses, cycloidal diffractive waveplates, axial diffractive waveplates, axicon diffractive waveplates, beam shaping diffractive waveplates, and arrays of diffractive waveplates; and
    one or more switching devices for selectively switching the propagation direction, phase profile, and optical power of said system of one or more diffractive waveplates to provide an electrically controlled diffraction property in reflected light; wherein the flat mirror and the one or more diffractive waveplates and the one or more switching devices form the basis of an optical communication system.

2. The optical communication system as in claim 1 wherein said laser light source is fiber coupled.

3. The optical communication system as in claim 1, wherein said one or more diffractive waveplates have an optical axis orientation that is modulated in one or both transverse directions parallel to a substrate.

4. The optical communication system as in claim 1 wherein said one or more switching devices for selectively switching the optical power of said optical communication system include variable phase retardation plates.

5. The optical communication system as in claim 4 wherein said one or more diffractive waveplates are deposited on a surface of at least one of the variable phase retardation plates.

6. The optical communication system as in claim 1, wherein a cylinder axes in alternating cylindrical diffractive waveplate lenses are rotated with respect to each other.

7. An optical communication system with multiple focal points comprising:
    a generally unpolarized and non-monochromatic laser light source;
    a system of one or more diffractive waveplates with switchable optical power for receiving the light from the generally unpolarized and non-monochromatic laser light source, said one or more diffractive wave plates are selected from a group consisting of diffractive waveplate lenses, cycloidal diffractive waveplates, axial diffractive waveplates, axicon diffractive waveplates, beam shaping diffractive waveplates, and arrays of diffractive waveplates;

a substrate in the optical communication system; and one or more switching devices for selectively switching the propagation direction, phase profile and optical power of said one or more diffractive waveplates, wherein the one or more diffractive waveplates and the substrate and the one or more switching devices provide controls for the optical communication system, wherein said one or more switching devices for selectively switching at least one of: the propagation direction, phase profile and the optical power of said optical communication system include variable phase retardation plates.

8. The optical communication system as in claim 1 wherein said one or more switching devices switch said one or more diffractive wave plates from an active state to a passive state so that optical beams are manipulated by the said one or more switching devices.

9. The optical communication system as in claim 1, wherein the laser light source is selected from the group consisting of: visible region, microwave region, infrared region, ultraviolet region and X-ray regions of the light spectrum.

10. The optical communication system as in claim 7 wherein said one or more switching devices switch said one or more diffractive wave plates from an active state to a passive state so that optical beams are manipulated by the said one or more switching devices.

11. The optical communication system as in claim 7, wherein the generally unpolarized and non-monochromatic laser light source is selected from the group consisting of: visible region, microwave region, infrared region, ultraviolet region and X-ray region of the light spectrum.

* * * * *